US012788508B2

(12) United States Patent
Miller et al.

(10) Patent No.: US 12,788,508 B2
(45) Date of Patent: *Nov. 10, 2026

(54) SYSTEMS AND METHODS FOR CONTROLLING A ROBOTIC MANIPULATOR OR ASSOCIATED TOOL

(71) Applicant: INTUITIVE SURGICAL OPERATIONS, INC., Sunnyvale, CA (US)

(72) Inventors: Daniel N. Miller, Fremont, CA (US); Dinesh Rabindran, San Jose, CA (US); Kollin M. Tierling, Los Altos Hills, CA (US)

(73) Assignee: INTUITVE SURGICAL OPERATIONS, INC., Sunnyvale, CA (US)

(*) Notice: Subject to any disclaimer, the term of this patent is extended or adjusted under 35 U.S.C. 154(b) by 101 days.

This patent is subject to a terminal disclaimer.

(21) Appl. No.: 18/904,838

(22) Filed: Oct. 2, 2024

(65) Prior Publication Data

US 2025/0025247 A1 Jan. 23, 2025

Related U.S. Application Data

(63) Continuation of application No. 18/301,905, filed on Apr. 17, 2023, now Pat. No. 12,133,700, which is a (Continued)

(51) Int. Cl.
*B25J 13/08* (2006.01)
*A61B 34/30* (2016.01)
(Continued)

(52) U.S. Cl.
CPC .............. *A61B 34/30* (2016.02); *A61B 34/37* (2016.02); *B25J 9/1607* (2013.01); *B25J 9/1638* (2013.01);
(Continued)

(58) Field of Classification Search
CPC ......... A61B 34/30; A61B 34/37; A61B 34/74; A61B 34/76; A61B 2034/2048;
(Continued)

(56) References Cited

U.S. PATENT DOCUMENTS 6,728,599 B2 4/2004 Yulun et al.
6,785,593 B2 8/2004 Wang et al.
(Continued)

FOREIGN PATENT DOCUMENTS

EP 1915963 A1 4/2008
EP 2835227 A1 2/2015
(Continued)

OTHER PUBLICATIONS

An et al., Model-based control of a direct drive arm. I. Building models, 1988, IEEE, p. 1374-1379 (Year: 1988).*
(Continued)

*Primary Examiner* — Mcdieunel Marc
(74) *Attorney, Agent, or Firm* — Haynes & Boone, LLP.

(57) ABSTRACT

A system comprises a robotic manipulator for control of motion of a medical tool. The robotic manipulator including a joint and a link connected to the joint. The link is configured to connect to the medical tool. A processing unit of the system is configured to receive first data from an encoder of the joint. A first tool tip estimate of a first parameter of a tool tip coupled at a distal end of the medical tool is generated using the first data. The first parameter of the tool tip is a position or a velocity of the tool tip. Second data is received from a sensor system located at a sensor portion of the link or the medical tool. The joint is controlled based on a first difference between the first tool tip estimate and a second tool tip estimate generated using the first and second data.

20 Claims, 9 Drawing Sheets

Related U.S. Application Data continuation of application No. 17/186,391, filed on Feb. 26, 2021, now Pat. No. 11,653,987, which is a continuation of application No. 16/495,484, filed as application No. PCT/US2018/060129 on Nov. 9, 2018, now Pat. No. 10,952,801.

(60) Provisional application No. 62/584,377, filed on Nov. 10, 2017.

(51) Int. Cl.

*A61B 34/37* (2016.01)
*B25J 9/16* (2006.01)
*B25J 15/00* (2006.01)
*A61B 34/00* (2016.01)
*A61B 34/20* (2016.01)
*A61B 90/00* (2016.01)

(52) U.S. Cl.

CPC ............ *B25J 9/1641* (2013.01); *B25J 13/08* (2013.01); *B25J 15/0019* (2013.01); *A61B 2034/2059* (2016.02); *A61B 2034/301* (2016.02); *A61B 34/74* (2016.02); *A61B 34/76* (2016.02); *A61B 2090/066* (2016.02)

(58) Field of Classification Search

CPC .... A61B 2034/2051; A61B 2034/2055; A61B 2034/2059; A61B 2034/2061; A61B 2034/2065; A61B 2034/301; A61B 2090/066; A61B 2090/0818; B25J 9/1607; B25J 9/1638; B25J 9/1641; B25J 13/08; B25J 15/0019

See application file for complete search history.

(56) References Cited

U.S. PATENT DOCUMENTS

| | | | | |
|---|---|---|---|---|
| 6,799,088 | B2 | 9/2004 | Wang et al. | |
| 6,836,703 | B2 | 12/2004 | Wang et al. | |
| 6,839,612 | B2 | 1/2005 | Sanchez et al. | |
| 6,892,112 | B2 | 5/2005 | Wang et al. | |
| 6,999,852 | B2 | 2/2006 | Green | |
| 7,248,944 | B2 | 7/2007 | Green | |
| 7,359,782 | B2 | 4/2008 | Breed | |
| 7,386,365 | B2 | 6/2008 | Nixon | |
| 7,778,733 | B2 | 8/2010 | Nowlin et al. | |
| 8,010,286 | B2 | 8/2011 | Templeton et al. | |
| 8,792,963 | B2 | 7/2014 | Zhao et al. | |
| 8,864,752 | B2 | 10/2014 | Diolaiti et al. | |
| 9,079,305 | B2 | 7/2015 | Williamson et al. | |
| 9,119,652 | B2 | 9/2015 | Prisco et al. | |
| 9,283,049 | B2 | 3/2016 | Diolaiti et al. | |
| 9,717,563 | B2 * | 8/2017 | Tognaccini | A61B 1/018 |
| 10,258,425 | B2 * | 4/2019 | Mustufa | A61B 34/37 |
| 10,507,066 | B2 * | 12/2019 | DiMaio | A61B 34/30 |
| 10,952,801 | B2 * | 3/2021 | Miller | A61B 34/30 |
| 11,026,755 | B2 * | 6/2021 | Weir | A61B 17/07207 |
| 11,653,987 | B2 | 5/2023 | Miller et al. | |
| 11,850,011 | B2 * | 12/2023 | Staunton | A61B 34/30 |
| 12,029,518 | B2 * | 7/2024 | Tanaka | A61B 90/361 |
| 12,133,700 | B2 * | 11/2024 | Miller | A61B 34/30 |
| 12,357,400 | B2 * | 7/2025 | Itkowitz | A61B 34/30 |
| 12,484,989 | B2 * | 12/2025 | Brubaker | A61B 90/361 |
| 2001/0013764 | A1 | 8/2001 | Blumenkranz et al. | |
| 2006/0265120 | A1 | 11/2006 | Coleman et al. | |
| 2007/0057842 | A1 | 3/2007 | Coleman et al. | |
| 2007/0138992 | A1 | 6/2007 | Prisco et al. | |
| 2007/0151389 | A1 | 7/2007 | Prisco et al. | |
| 2007/0287992 | A1 | 12/2007 | Diolaiti et al. | |
| 2009/0088634 | A1 | 4/2009 | Zhao et al. | |
| 2009/0088773 | A1 | 4/2009 | Zhao et al. | |
| 2009/0088897 | A1 | 4/2009 | Zhao et al. | |
| 2009/0171371 | A1 | 7/2009 | Nixon et al. | |
| 2011/0218673 | A1 | 9/2011 | Oga et al. | |
| 2014/0052298 | A1 | 2/2014 | Hourtash et al. | |
| 2014/0276950 | A1 | 9/2014 | Smaby et al. | |
| 2015/0120053 | A1 | 4/2015 | Motoyoshi | |
| 2015/0313679 | A1 | 11/2015 | Fukushima et al. | |
| 2016/0030119 | A1 | 2/2016 | Devengenzo et al. | |
| 2016/0301845 | A1 | 10/2016 | Bell et al. | |
| 2017/0108929 | A1 | 4/2017 | Sinko et al. | |
| 2018/0132850 | A1 | 5/2018 | Leimbach et al. | |
| 2019/0143506 | A1 | 5/2019 | Rabindran et al. | |
| 2019/0143513 | A1 | 5/2019 | Rabindran et al. | |
| 2021/0354286 | A1 | 11/2021 | Dimaio et al. | |
| 2022/0080589 | A1 * | 3/2022 | Rabindran | A61B 34/37 |
| 2023/0248454 | A1 | 8/2023 | Miller et al. | |
| 2023/0286147 | A1 * | 9/2023 | Rabindran | B25J 9/1664 |

FOREIGN PATENT DOCUMENTS

| | | | |
|---|---|---|---|
| WO | WO-2012158458 | A2 | 11/2012 |
| WO | WO-2015142956 | A1 | 9/2015 |
| WO | WO-2016032902 | A1 | 3/2016 |
| WO | WO-2016069661 | A1 | 5/2016 |

OTHER PUBLICATIONS

Swevers et al., Dynamic Model Identification for Industrial Robots, 2007, IEEE, p. 1-14 (Year: 2007).*

An et al., Estimation of inertial parameters of rigid body links of manipulators, 1995, IEEE, p. 1-6 (Year: 1995).*

Mukerjee et al., Self-calibration in robot manipulators, 1985, IEEE, p. 1050-1057 (Year: 1985).*

Alkkiomaki O., et al., "Online Trajectory Following With Position Based Force/vision Control," IEEE, Jun. 2009, pp. 1-6.

An C.H., et al., "Model-based Control of a Direct Drive Arm. I. Building Models," IEEE, Apr. 1988, pp. 1374-1379.

Axelsson P., et al., "He-Controller Design Methods Applied to One Joint of a Flexible Industrial Manipulator," 19th IFAC World Congress Cape Town, South Africa, Aug. 24-29, 2014, pp. 210-216.

Behi F., et al., "Parametric Identification for Industrial Manipulators Using Experimental Modal Analysis," IEEE Transactions on Robotics and Automation, vol. 7 (5), Oct. 1991, pp. 642-652.

Chen W., et al., "Direct Joint Space State Estimation in Robots with Multiple Elastic Joints," IEEE/ASME Transactions on Mechatronics, Apr. 2014, vol. 19 (2), pp. 697-706.

Chen X et al., "Pose Estimation of Robotic End-Effectors Under Low-Speed Motion Using EKF With Inertial and SE(3) measurements",2015 IEEE International Conference on Advanced Intelligent Mechatronics (AIM), IEEE, Jul. 7, 2015, pp. 1585-1590.

Du G., et al., "Online Serial Manipulator Calibration Based on Multisensory Process Via Extended Kalman and Particle Filters," IEEE, Mar. 2014, vol. 61 (12), pp. 6852-6859.

Extended European Search Report for Application No. EP18876581.2 mailed on Oct. 8, 2020, 10 pages.

Extended European Search Report for Application No. EP22188588.2, mailed on Feb. 1, 2023. 10 pages.

Hagn U., et al., "Telemanipulator for Remote Minimally Invasive Surgery: Requirements for a Light-Weight Robot for Both Open and Laparoscopic Surgery," IEEE Robotics & Automation Magazine, 2008, pp. 28-38.

Honegger M., et al., "Application of a Nonlinear Adaptive Controller to a 6 DOF Parallel Manipulator," IEEE International Conference on Robotics and Automation, Apr. 2000, pp. 1930-1935.

Hynes P., et al., "Uncalibrated Visual-Servoing of a Dual-Arm Robot for MIS Suturing," Biomedical Robotics and Biomechatronics, 2006, pp. 420-426.

Hynes P., et al., "Uncalibrated visual-servoing of a Dual-arm Robot for Surgical Tasks," International Symposium on Computational Intelligence in Robotics and Automation, Jun. 2005, pp. 151-156.

International Preliminary Report on Patentability for Application No. PCT/US2018/060129, mailed on May 22, 2020, 6 pages.

International Search Report and Written Opinion for Application No. PCT/US2018/060129, mailed on May 14, 2019, 10 pages (ISRG10670/PCT).

(56) References Cited

OTHER PUBLICATIONS

Newmann M., "Control of Posture and Tool Location Using a Single Force/torque Sensor," IEEE International Conference on Robotics and Automation, May 2001, pp. 3390-3395.
Roozing W et al., "Comparison of Open-Loop and Closed-loop Disturbance Observers for SeriesElastic Actuators", 2016 IEEE/RSJ International Conference on Intelligent Robots and Systems (IROS), IEEE, Oct. 9, 2016, pp. 3842-3847.
Vertut. J., and Coiffet. P., "Robot Technology: Teleoperation and Robotics Evolution and Development," English translation, Prentice-Hall, Inc., Inglewood Cliffs, NJ, USA 1986, vol. 3A, 332 pages.
Vikas V., et al., "Joint Angle Measurement Using Strategically Placed Accelerometers and Gyroscope," Journal of Mechanisms and Robotics, Transactions of the ASME, vol. 8, May 2016, pp. 021003-1-021003-7.
Xiao D., et al., "Intelligent Robotic Manipulation With Hybrid Position/force Control in an Uncalibrated Workspace," Proceedings. 1998 IEEE International Conference on Robotics and Automation, May 1998, pp. 1671-1676.
Zemiti N., et al., "Mechatronic Design of a New Robot for Force Control in Minimally Invasive Surgery," IEEE/ASME Transactions on Mechatronics, Apr. 2007, vol. 12 (2), pp. 143-153.
Zuhars J., et al., "Nonhomogeneous Material Milling Using a Robot Manipulator With Force Controlled Velocity," IEEE International Conference on Robotics and Automation, 1995, pp. 1461-1467.
Extended European Search Report for Application No. EP25205116.4, mailed on Dec. 22, 2025, 9 pages.

* cited by examiner

SYSTEMS AND METHODS FOR CONTROLLING A ROBOTIC MANIPULATOR OR ASSOCIATED TOOL

CROSS-REFERENCE TO RELATED APPLICATIONS

This patent application is a continuation of U.S. patent application Ser. No. 18/301,905, filed Apr. 17, 2023, which is a continuation of U.S. patent application Ser. No. 16/495,484, filed Sep. 19, 2019, which is the U.S. national phase of International Application No. PCT/US2018/060129, filed Nov. 9, 2018, which designated the U.S. and claims priority to and benefit of the filing date of U.S. Provisional Patent Application 62/584,377, filed Nov. 10, 2017, entitled "SYSTEMS AND METHODS FOR CONTROLLING A ROBOTIC MANIPULATOR OR ASSOCIATED TOOL," which are incorporated by reference herein in their entirety.

FIELD

The present disclosure is directed to systems and methods for performing a robotic procedure, and more particularly to systems and methods for controlling more particularly to systems and methods for controlling a robotic manipulator or a tool associated with a robotic manipulator

BACKGROUND

Robotic manipulator assemblies can be operated to control motion of tools in a workspace. For example, such robotic manipulators can be used to perform non-medical and medical procedures. As a specific example, teleoperated surgical manipulators can be used to perform minimally invasive medical procedures.

It is desirable in medical techniques are intended to reduce the amount of tissue that is damaged during medical procedures, thereby reducing patient recovery time, discomfort, and harmful side effects. For example, minimally invasive techniques may be performed through natural orifices in a patient anatomy or through one or more incisions. Through these natural orifices or incisions, clinicians may insert medical tools to reach a target tissue location. Minimally invasive medical tools include tools such as therapeutic tools, diagnostic tools, and surgical tools. Minimally invasive medical tools may also include imaging tools such as endoscopic tools that provide a user visualization within the patient anatomy.

Robotic manipulators may be teleoperated or otherwise computer-assisted. For example, a tool may be held by a robotic manipulator assembly for performing a procedure. However, flexibility in such a robotic manipulator assembly and the tool may cause under-damped vibrations with undesirably long settling times. Flexibility (compliance) may be used to measure physical compliance, mechanical compliance, structural compliance, and the ability to deflect under load. In examples where the robotic manipulator assembly (including its base, joints, and links) has a relatively large flexibility and/or has relatively large link masses or inertias, motions commanded of the robotic manipulator assembly or external disturbances may cause such vibrations. As such, a combination of physical parameters including compliance (e.g., physical, mechanical, and structural compliance), damping (e.g., physical damping including viscous damping, where viscous damping elements (e.g., lubricant friction) resist motion with forces proportional to the velocity of motion), and mass/inertia results in a low mechanical resonance with less than desired damping. During a procedure, commanded motions or external disturbances may excite these low mechanical resonances causing undesirable vibrations. While performing a procedure, such vibrations experienced at the tool tip or another point of control on the robot manipulator may result in inferior system performance. For example, such vibrations may make it difficult for the computer-assisted system to achieve or follow commanded trajectories for the tool.

Such vibrations may negatively affect control in all types of robotic systems, including medical robotic systems. In a medical robotic example, such vibrations may make it difficult for a medical robotic system to perform the commanded manipulations of tissue, movement of imaging systems, insertion of needles, application of sutures, etc. For a further example, in some implementations, the tool is moved around a remote center of motion (also referred to as "remote center") during part or all of a procedure. In some instances, the vibrations may cause the remote center of motion to move during surgery or other medical procedures, and impart undesirable forces on the body wall at the port of entry. The vibrations may cause the actual pose or motion of the tool (or a manipulator holding the tool) to deviate from the commanded posed or motion to such an extent that the tool (or manipulator) acts as if the remote center has moved beyond a predetermined tolerance from its defined position. That is, the range of location of the virtual fulcrum associated with the motion of the manipulator and/or the tool is caused by the vibrations to exceed a tolerance amount from a defined remote center of motion.

Thus, systems and methods are desired to provide better control of robotic systems, such as better control of a manipulator of a robotic system by mitigating undesirable vibrations, the tip of a tool held by the robotic system, and the motion of the manipulator or a tool supported by the manipulator about the remote center of motion of the tool.

SUMMARY

The embodiments of the invention are summarized by the claims that follow below.

In one illustrative embodiment, a system comprises a robotic manipulator configured for control of motion of a medical tool, the robotic manipulator including a joint and a link connected to the joint. The link is configured to connect to the medical tool. The system further comprises a processing unit including one or more processors. The processing unit is configured to receive first data from an encoder of the joint, and generate a first tool tip estimate of a first parameter of a tool tip coupled at a distal end of the medical tool using the first data, wherein the first parameter of the tool tip is a position or a velocity of the tool tip. The processing unit is also configured to receive second data from a sensor system located at a sensor portion of the link or at the medical tool; generate a second tool tip estimate of the first parameter of the tool tip using the first and second data; and control the joint based on a first difference between the first and second tool tip estimates.

In another illustrative embodiment, a method includes receiving first data from an encoder of a joint of a robotic manipulator. The robotic manipulator a link connected to the joint. A medical tool is connected to the link. A first tool tip estimate of a first parameter of a tool tip coupled at a distal end of the medical tool is generated using the first data. The first parameter of the tool tip is a position or a velocity of the tool tip. Second data from a sensor system located at a sensor portion of the link or at the medical tool is received. A second tool tip estimate of the first parameter of the tool tip is generated using the first and second data. The joint is controlled based on a first difference between the first and second tool tip estimates.

In another illustrative embodiment, a non-transitory machine-readable medium comprises a plurality of machine-readable instructions which, when executed by one or more processors, are adapted to cause the one or more processors to perform a method. The method includes receiving first data from an encoder of a joint of a robotic manipulator. The robotic manipulator a link connected to the joint. A medical tool is connected to the link. A first tool tip estimate of a first parameter of a tool tip coupled at a distal end of the medical tool is generated using the first data. The first parameter of the tool tip is a position or a velocity of the tool tip. Second data from a sensor system located at a sensor portion of the link or at the medical tool is received. A second tool tip estimate of the first parameter of the tool tip is generated using the first and second data. The joint is controlled based on a first difference between the first and second tool tip estimates.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

Figure 2A:
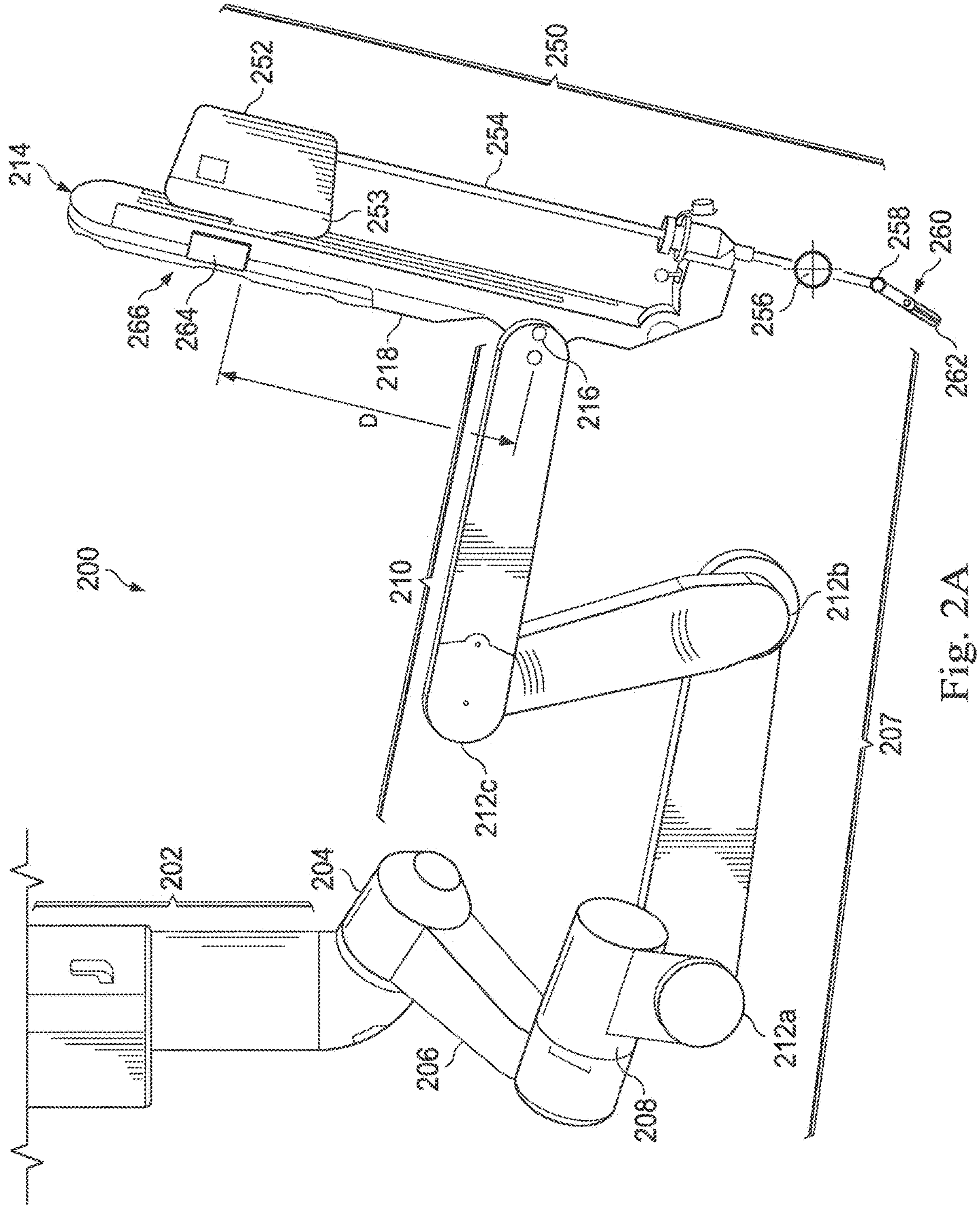
Figure 2B:
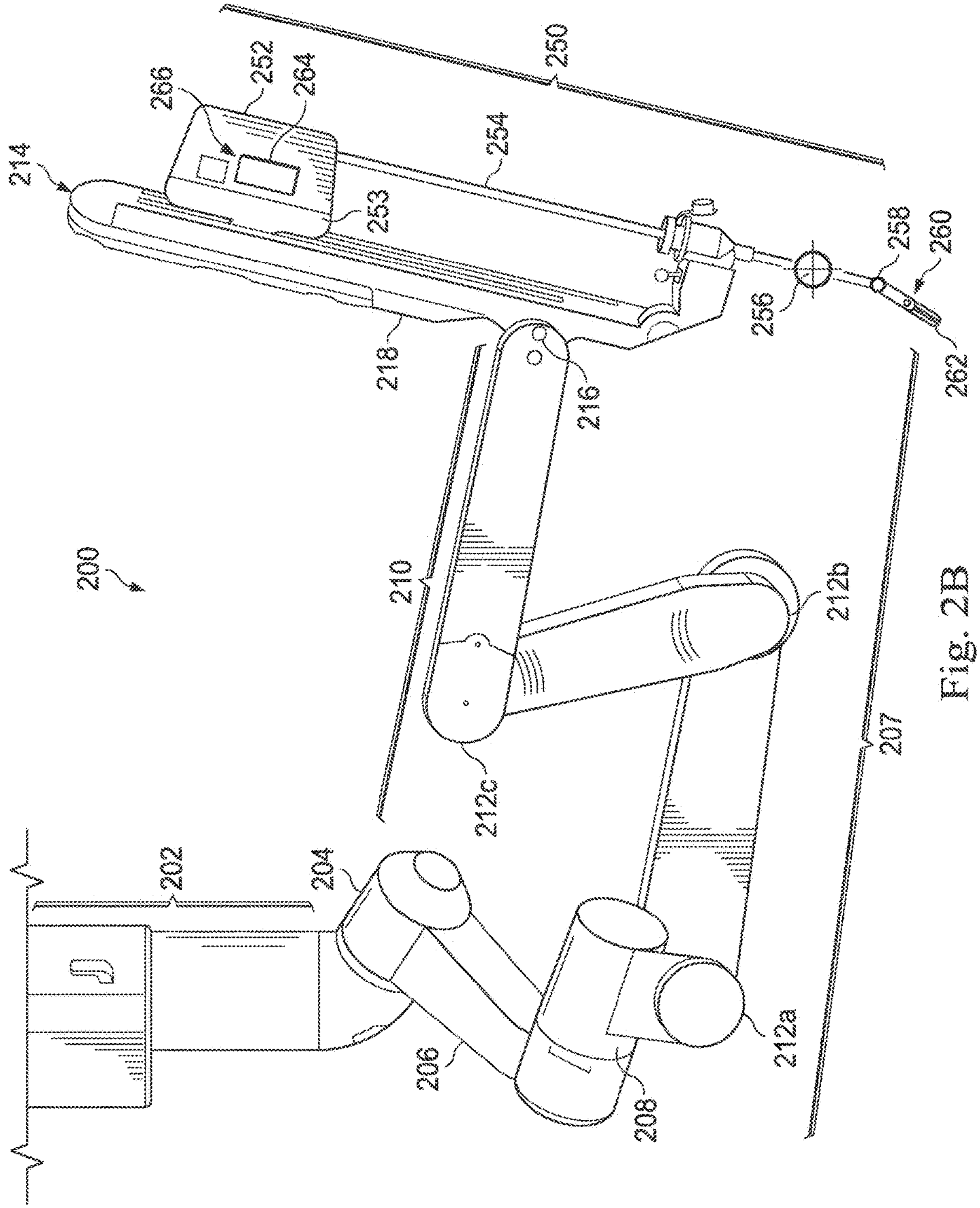
Figure 2C:
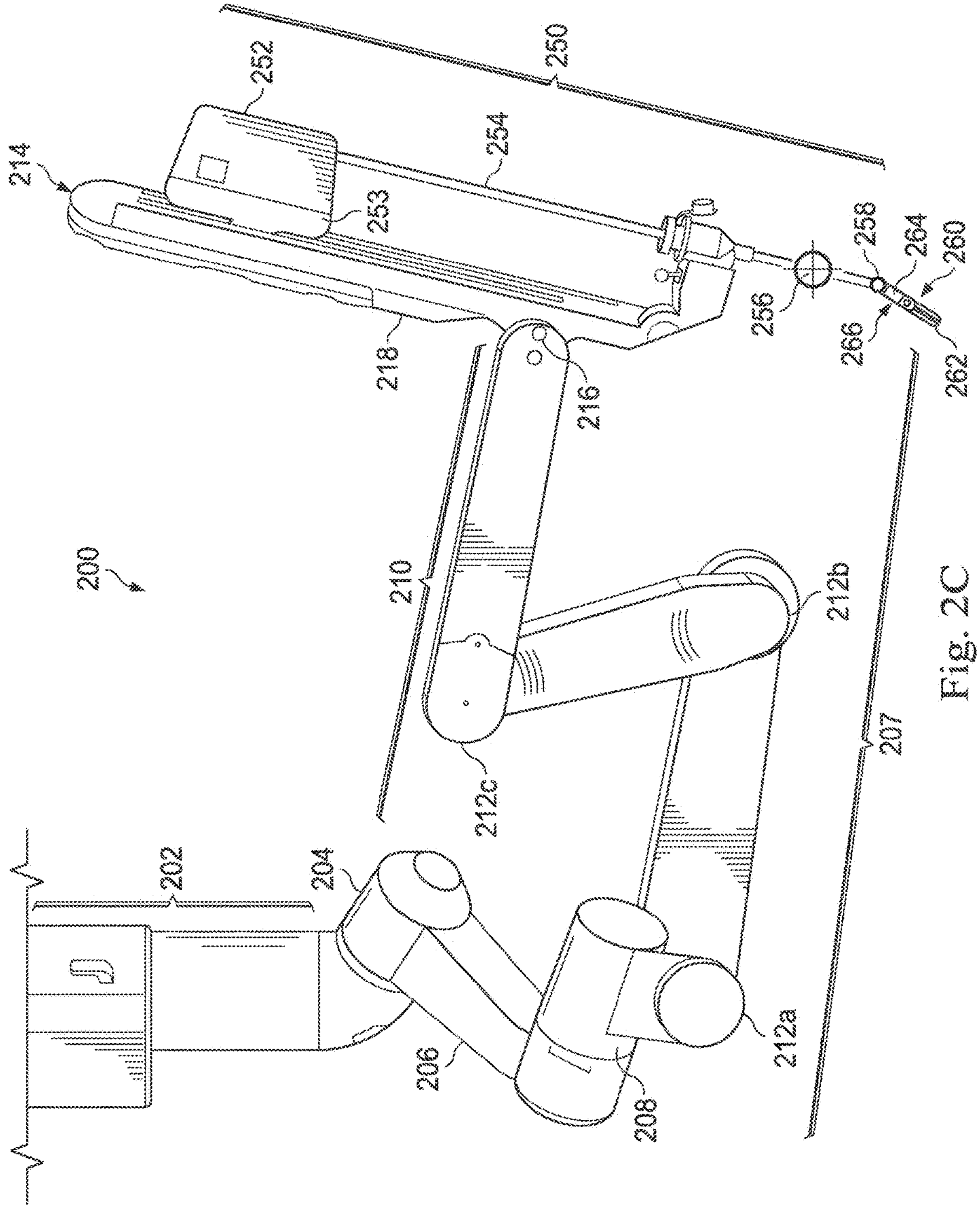

FIGS. 2A, 2B, and 2C illustrate various embodiments of a robotic arm assembly with a load-side sensor, in accordance with the present disclosure.

Figure 3:
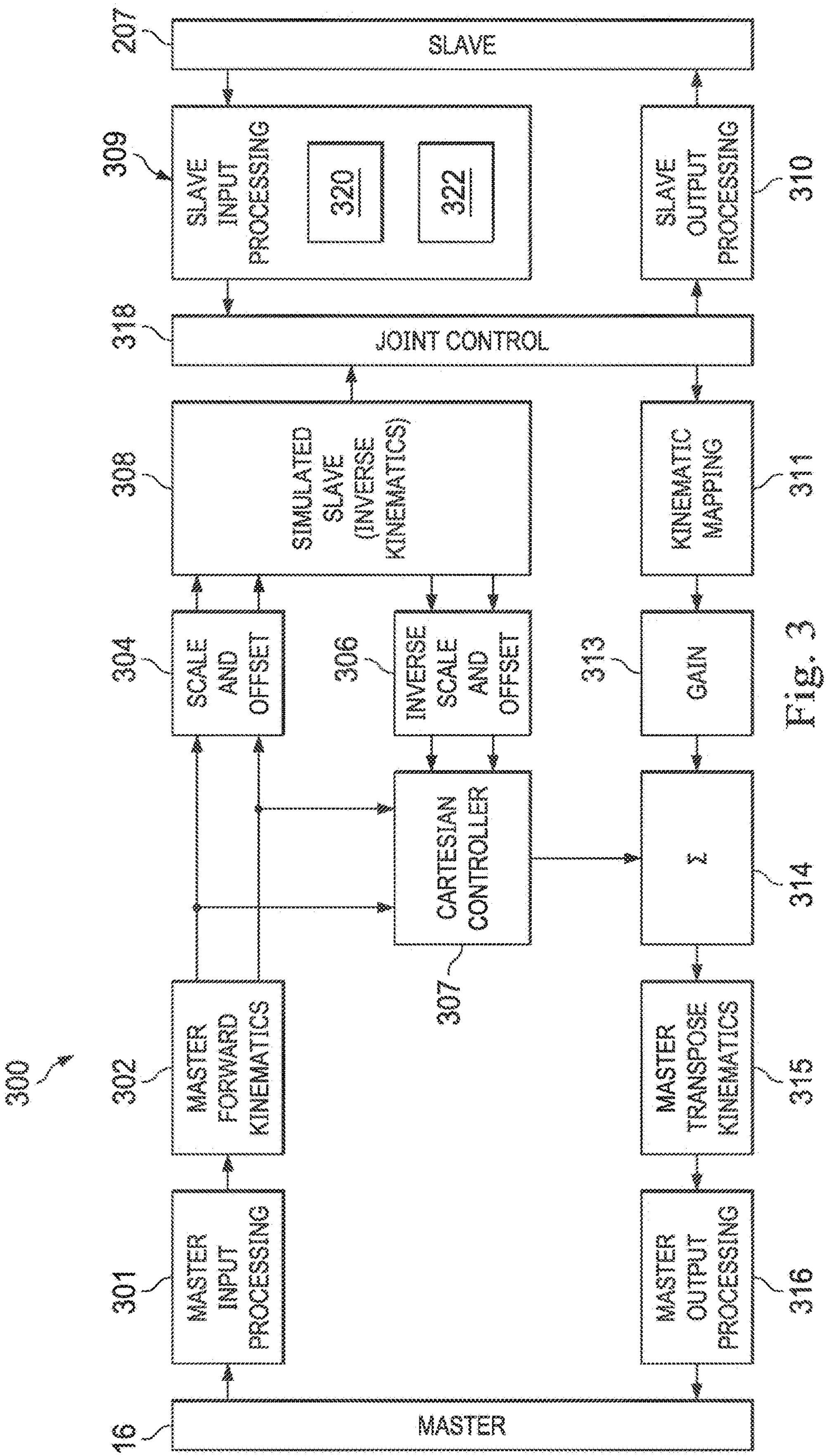

FIG. 3 illustrates a block diagram of a master/slave control system in accordance with an embodiment of the present disclosure.

Figure 4A:
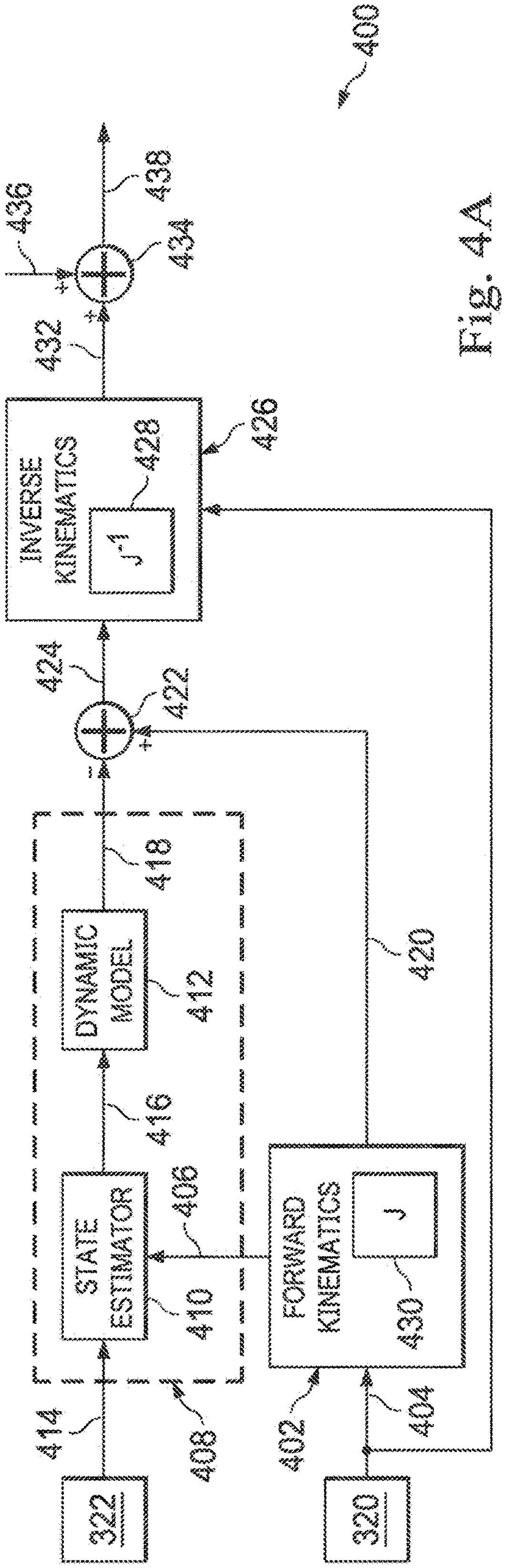

FIG. 4A illustrates a block diagram of a slave joint controller in accordance with an embodiment of the present disclosure.

Figure 4B:
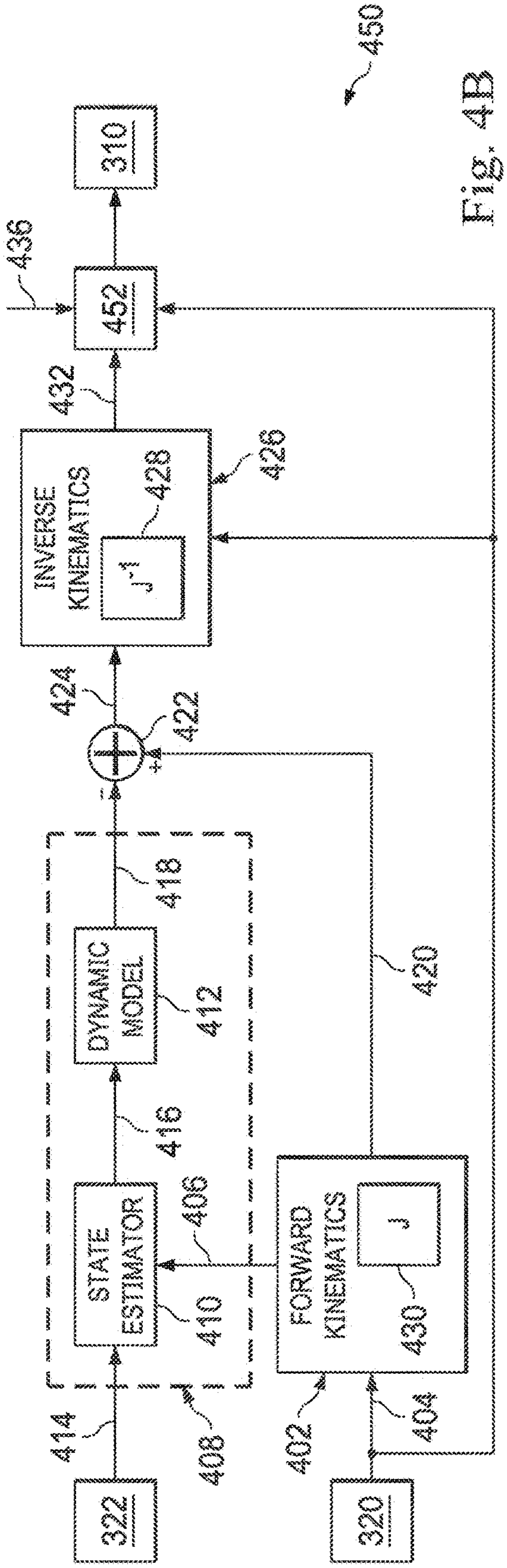

FIG. 4B illustrates a block diagram of a slave joint controller in accordance with an embodiment of the present disclosure.

Figure 5:
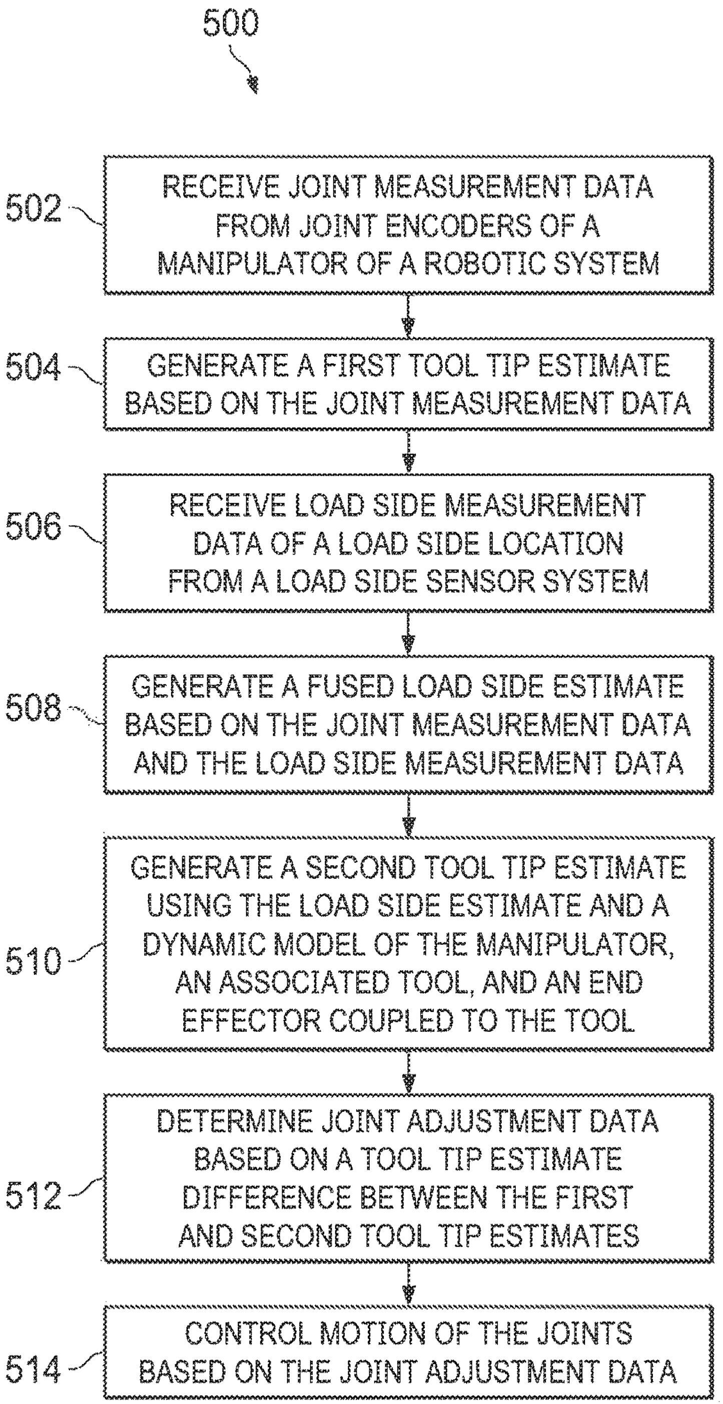

FIG. 5 is a flowchart providing a method for controlling a manipulator and an associated tool according to an embodiment of the present disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances, well-known methods, procedures, components, and circuits have not been described in detail so as not to unnecessarily obscure aspects of the embodiments of the invention.

Any alterations and further modifications to the described devices, tools, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances, the same reference numbers are used throughout the drawings to refer to the same or like parts.

Although some of the examples described herein often refer to medical procedures and medical tools, the techniques disclosed also apply to non-medical procedures and non-medical tools. For example, the tools, systems, and methods described herein may be used for non-medical purposes including industrial uses, general robotic uses, manipulation of non-tissue work pieces, and/or cosmetic improvements. Other non-surgical applications include use on tissue removed from human or animal anatomies (without return to a human or animal anatomy), or on human or animal cadavers.

The embodiments below will describe various tools and portions of tools in terms of their state in three-dimensional space. As used herein, the term "position" refers to the location of an object or a portion of an object in a three-dimensional space (e.g., three degrees of translational freedom that can be described using changes in Cartesian X, Y, Z coordinates, such as along Cartesian X, Y, Z axes). As used herein, the term "orientation" refers to the rotational placement of an object or a portion of an object (three degrees of rotational freedom—e.g., which can be described using roll, pitch, and yaw). As used herein, the term "pose" refers to the position of an object or a portion of an object in at least one degree of translational freedom, and to the orientation of that object or that portion of that object in at least one degree of rotational freedom. For an asymmetric, rigid body in a three-dimensional space, a full pose can be described with six total degrees of freedom.

Figure 1A:
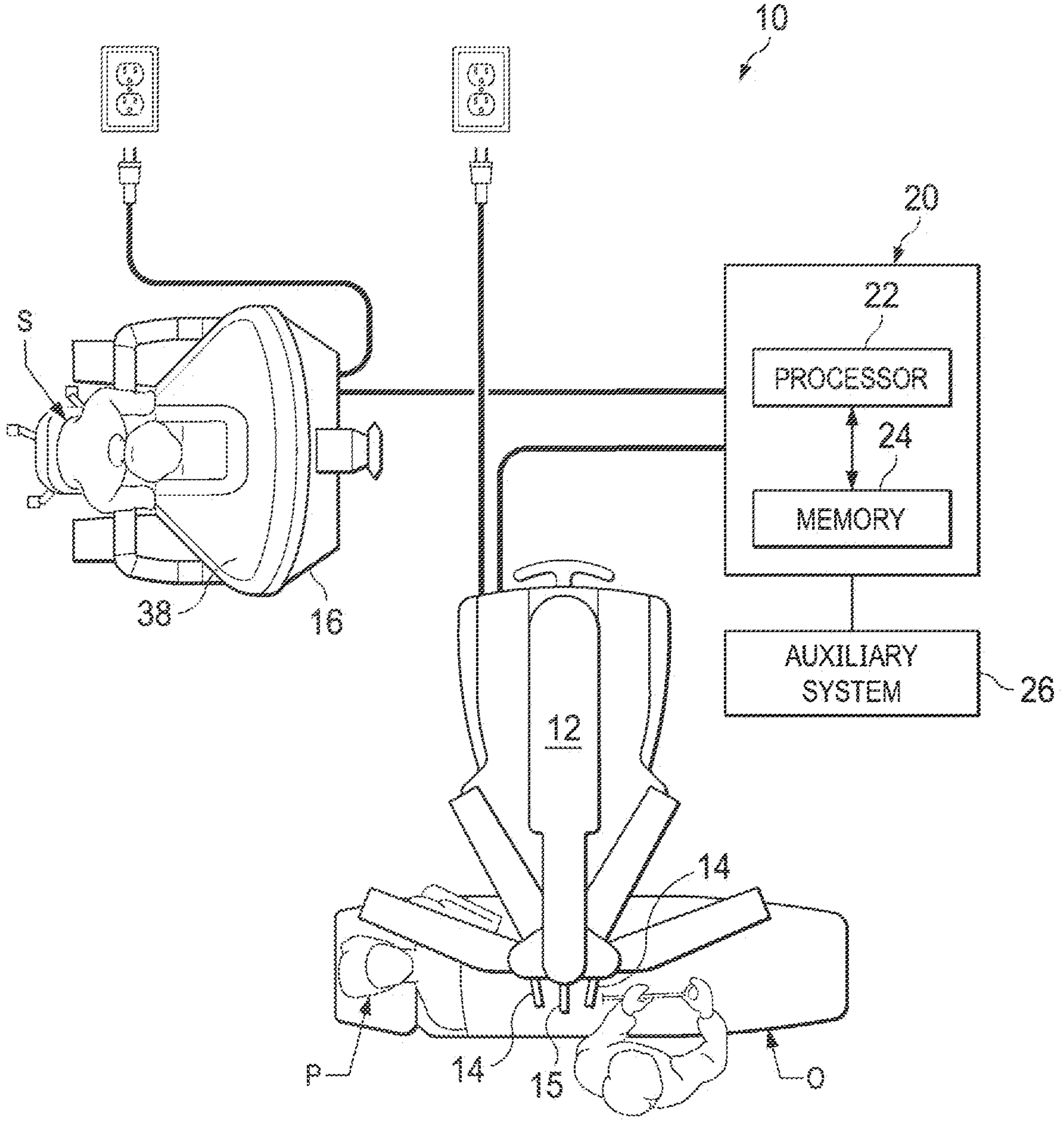
FIG. 1A is a schematic view of a robotic medical system, in accordance with an embodiment of the present disclosure.

Referring to FIG. 1A of the drawings, an example robotic system is shown. Specifically, in FIG. 1A, a computer-aided, robotic medical system that may be teleoperated and used in, for example, medical procedures including diagnostic, therapeutic, or surgical procedures, is generally indicated by the reference numeral 10. As will be described, the teleoperational systems of this disclosure are under the teleoperational control of an operator. In some embodiments, manipulators or other parts of a robotic system may be controlled directly through manual interaction with the manipulators (or the other parts) themselves. Thus, "teleoperated manipulators" as used in this application include manipulators that can be controlled only through teleoperation, and manipulators that can be controlled through teleoperation and through direct manual control. Further, in some embodiments, a non-teleoperational or teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures.

As shown in FIG. 1A, the teleoperational medical system 10 generally includes a manipulator assembly 12 mounted to or near an operating table O on which a patient P is positioned. The manipulator assembly 12 may be referred to as a patient side cart in this example, since it comprises a cart and is designed to be used next to a patient. A first medical instrument system 14 and a second medical instrument system 15 are operably coupled to the manipulator assembly 12. Within this disclosure, the first medical instrument system 14 may also be referred to as the medical tool 14, and the second medical instrument system 15 may also be referred to as the medical tool 15. Further, within the remainder of this disclosure, the second medical instrument system 15 is often described as having imaging capabilities for case of explanation; in those case, the second medical instrument system 15 may also be referred to as the imaging system 15. However, it is contemplated that none, either, or both medical instruments 14 and 15 may have non-imaging capabilities and/or imaging capabilities. The imaging system 15 may comprise an endoscopic imaging system using optical imaging technology, or comprise another type of imaging system using other technology (e.g. ultrasonic, fluoroscopic, etc.). An operator input system 16 allows an operator such as a surgeon or other type of clinician S to view images of or representing the procedure site and to control the operation of the medical tool 14 and/or the medical tool 15.

The operator input system 16 for the teleoperational medical system 10 may be "mechanically grounded" by being connected to a base with linkages such as to an operator's console, or it may be "mechanically ungrounded" and not be thus connected. As shown in FIG. 1A, the operator input system 16 is connected to an operator console that is usually located in the same room as operating table O during a surgical procedure. It should be understood, however, that the operator S can be located in a different room or a completely different building from the patient P. The operator input system 16 generally includes one or more control device(s) for controlling the medical tool 14. (The operator input system 16 is also referred to herein as "master manipulators" and "master input devices" and "input devices".) The control device(s) may include one or more of any number of a variety of input devices, such as hand grips, joysticks, trackballs, data gloves, trigger-guns, foot pedals, hand-operated controllers, voice recognition devices, touch screens, body motion or presence sensors, and the like. In some embodiments, the control device(s) will be provided with the same degrees of freedom as the medical tools of the robotic assembly to provide the operator with telepresence; that is, the operator is provided with the perception that the control device(s) are integral with the tools so that the operator has a sense of directly controlling tools as if present at the procedure site. In other embodiments, the control device(s) may have more or fewer degrees of freedom than the associated medical tools and still provide the operator with telepresence. In some embodiments, the control device (s) are manual input devices which move with six degrees of freedom, and which may also include an actuatable handle for actuating medical tools (for example, for closing grasping jaw end effectors, applying an electrical potential to an electrode, delivering a medicinal treatment, and the like).

The manipulator assembly 12 supports and manipulates the medical tool 14 while the operator S views the procedure site through the operator's console. An image of the procedure site can be obtained by the medical tool 15, such as via an imaging system comprising a monoscopic or stereoscopic endoscope, which can be manipulated by the manipulator assembly 12 to orient the medical tool 15. An electronics cart can be used to process the images of the procedure site for subsequent display to the operator S through the operator's console. The number of medical tools 14 used at one time will generally depend on the medical diagnostic or treatment (e.g. surgical) procedure and the space constraints within the operating room among other factors. The manipulator assembly 12 may include a kinematic structure of one or more non-servo controlled links (e.g., one or more links that may be manually positioned and locked in place) and a robotic manipulator. The manipulator assembly 12 includes a plurality of motors that drive inputs on the medical tools 14. These motors move in response to commands from the control system (e.g., control system 20). The motors include drive systems which when coupled to the medical tools 14 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the tool for grasping tissue in the jaws of a biopsy device or the like. The medical tools 14 may include end effectors having a single working member such as a scalpel, a blunt blade, a needle, an imaging sensor, an optical fiber, an electrode, etc. Other end effectors may include multiple working members, and examples include forceps, graspers, scissors, clip appliers, staplers, bipolar electrocautery instruments, etc.

The teleoperational medical system 10 also includes a control system 20. The control system 20 includes at least one memory 24 and at least one processor 22, and typically a plurality of processors, for effecting control between the medical tool 14, the operator input system 16, and other auxiliary systems 26 which may include, for example, imaging systems, audio systems, fluid delivery systems, display systems, illumination systems, steering control systems, irrigation systems, and/or suction systems. The control system 20 also includes programmed instructions (e.g., a computer-readable medium storing the instructions) to implement some or all of the methods described in accordance with aspects disclosed herein. While control system 20 is shown as a single block in the simplified schematic of FIG. 1A, the system may include two or more data processing circuits with one portion of the processing optionally being performed on or adjacent the manipulator assembly 12, another portion of the processing being performed at the operator input system 16, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 20 supports wireless communication protocols such as Bluetooth, IrDA, HomeRF, IEEE 802.11, DECT, and Wireless Telemetry.

In some embodiments, the control system 20 may include one or more servo controllers that receive force and/or torque feedback from the medical tool 14 or from the manipulator assembly 12. Responsive to the feedback, the servo controllers transmit signals to the operator input system 16. The servo controller(s) may also transmit signals instructing manipulator assembly 12 to move the medical tool(s) 14 and/or 15 which extends into an internal procedure site within the patient body via openings in the body. Any suitable conventional or specialized controller may be used. A controller may be separate from, or integrated with, manipulator assembly 12. In some embodiments, the controller and teleoperational assembly are provided as part of an integrated system such as a teleoperational arm cart positioned proximate to the patient's body during the medical procedure.

The control system 20 can be coupled to the medical tool 15 and can include a processor to process captured images for subsequent display, such as to an operator using the operator's console or wearing a head-mounted display system, to one or more stationary or moveable monitors near the control system, or on another suitable display located locally and/or remotely. For example, where a stereoscopic endoscope is used, the control system 20 can process the captured images to present the operator with coordinated stereo images of the procedure site. Such coordination can include alignment between the stereo images and can include adjusting the stereo working distance of the stereoscopic endoscope.

In alternative embodiments, the robotic system may include more than one manipulator assembly and/or more than one operator input system. The exact number of manipulator assemblies will depend on the surgical procedure and the space constraints within the operating room, among other factors. The operator input systems may be collocated, or they may be positioned in separate locations. Multiple operator input systems allow more than one operator to control one or more manipulator assemblies in various combinations.

Figure 1B:
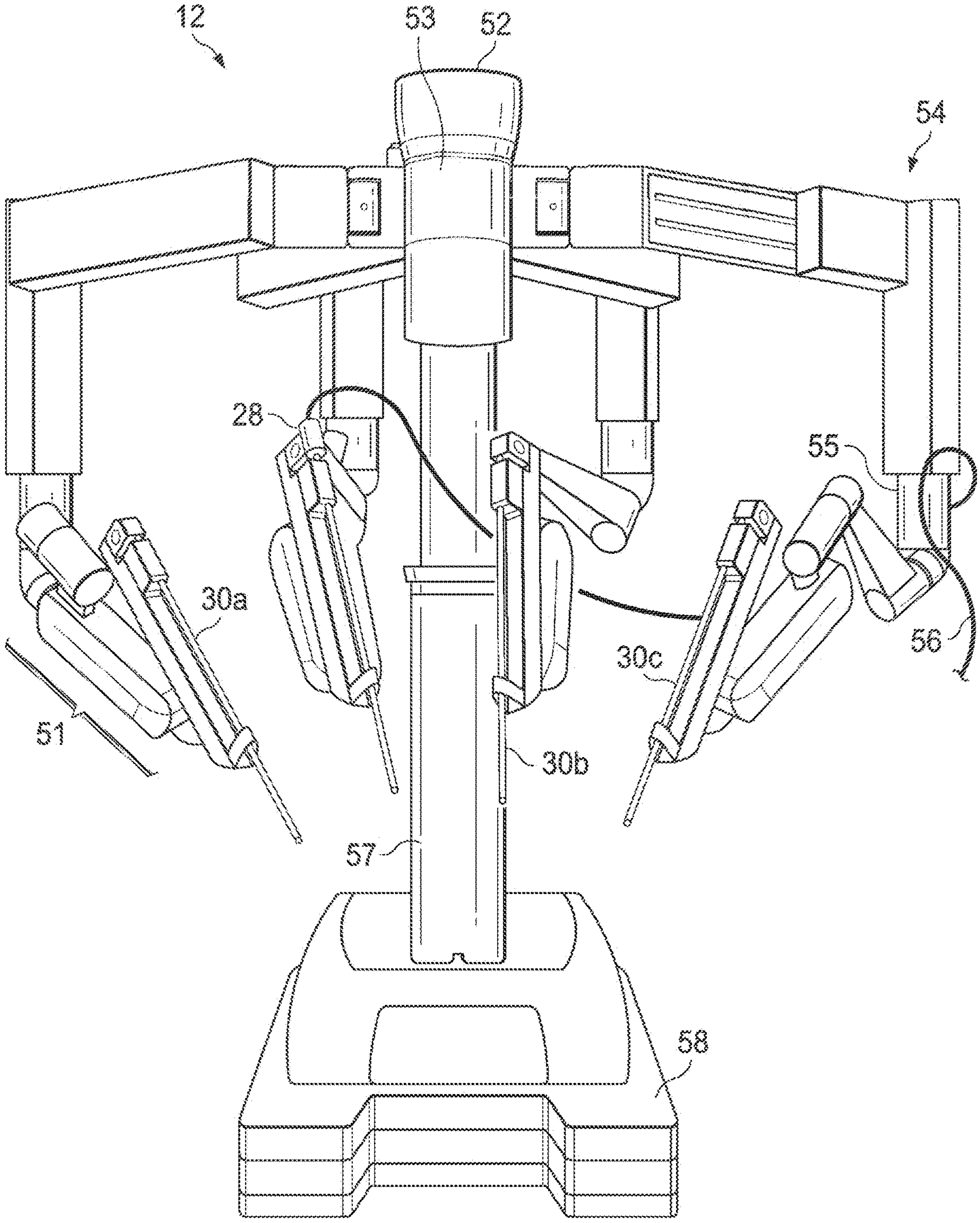
FIG. 1B is a perspective view of a manipulator assembly, in accordance with an embodiment of the present disclosure.

FIG. 1B is a perspective view of one embodiment of a manipulator assembly 12 that is configured in the form of a cart that is located near the patient during a medical procedure. Thus, this teleoperational assembly of FIG. 1B may also be referred to as a patient side cart. The manipulator assembly 12 shown provides for the manipulation of three medical tools 30*a*, 30*b*, 30*c* (e.g., medical tool 14) and a medical tool 28 including an imaging device (e.g., medical tool 15), such as a stereoscopic endoscope used for the capture of images of the work piece or of the site of the procedure (also called "work site"). The medical tool 28 may transmit signals over a cable 56 to the control system 20. Manipulation is provided by robotic manipulators having a number of joints. The medical tool 28 and the surgical tools 30*a-c* can be positioned and manipulated through incisions in, or natural orifices of, the patient so that a kinematic remote center is maintained at the incisions or natural orifices. Images of the work site can include images of the distal ends of the surgical tools 30*a-c* when they are positioned within the field-of-view of the medical tool 28.

The manipulator assembly 12 includes a drivable base 58. The drivable base 58 is connected to a telescoping column 57, which allows for adjustment of the height of the arms 54 (also called "manipulators 54"). The arms 54 may include a rotating joint 55 that both rotates and translates parallel to the column 57. The arms 54 may be connected to an orienting platform 53. The orienting platform 53 may be capable of 360 degrees of rotation. The manipulator assembly 12 may also include a telescoping horizontal cantilever 52 for moving the orienting platform 53 in a horizontal direction.

In the present example, each of the arms 54 includes a manipulator arm portion 51. The manipulator arm portion 51 may connect directly to a medical tool 14. The manipulator arm portion 51 may be teleoperatable. In some examples, the arms 54 connecting to the orienting platform are not teleoperatable. Rather, such arms 54 are positioned as desired before the operator S begins operation with the teleoperative components.

Endoscopic and other imaging systems (e.g., medical tool 15) may be provided in a variety of configurations, including ones having rigid or flexible structures. Rigid endoscopes include a rigid tube housing a relay lens system for transmitting an image from a distal end to a proximal end of the endoscope. Flexible endoscopes transmit images using one or more flexible optical fibers. Digital image based endoscopes may have a "chip on the tip" design in which a distal digital sensor such as a one or more charge-coupled device (CCD) or a complementary metal oxide semiconductor (CMOS) device store image data. Endoscopic imaging systems may also utilize other imaging technology such as ultrasonic, infrared, and fluoroscopic technologies. Endoscopic imaging systems may provide two- or three-dimensional images to the viewer. Two-dimensional images may provide limited depth perception. Three-dimensional stereo endoscopic images may provide the viewer with more accurate depth perception. Stereo endoscopic tools employ stereo cameras to capture stereo images of the patient anatomy. An endoscopic tool may be a fully sterilizable assembly with the endoscope cable, handle and shaft all rigidly coupled and hermetically sealed.

Figure 1C:
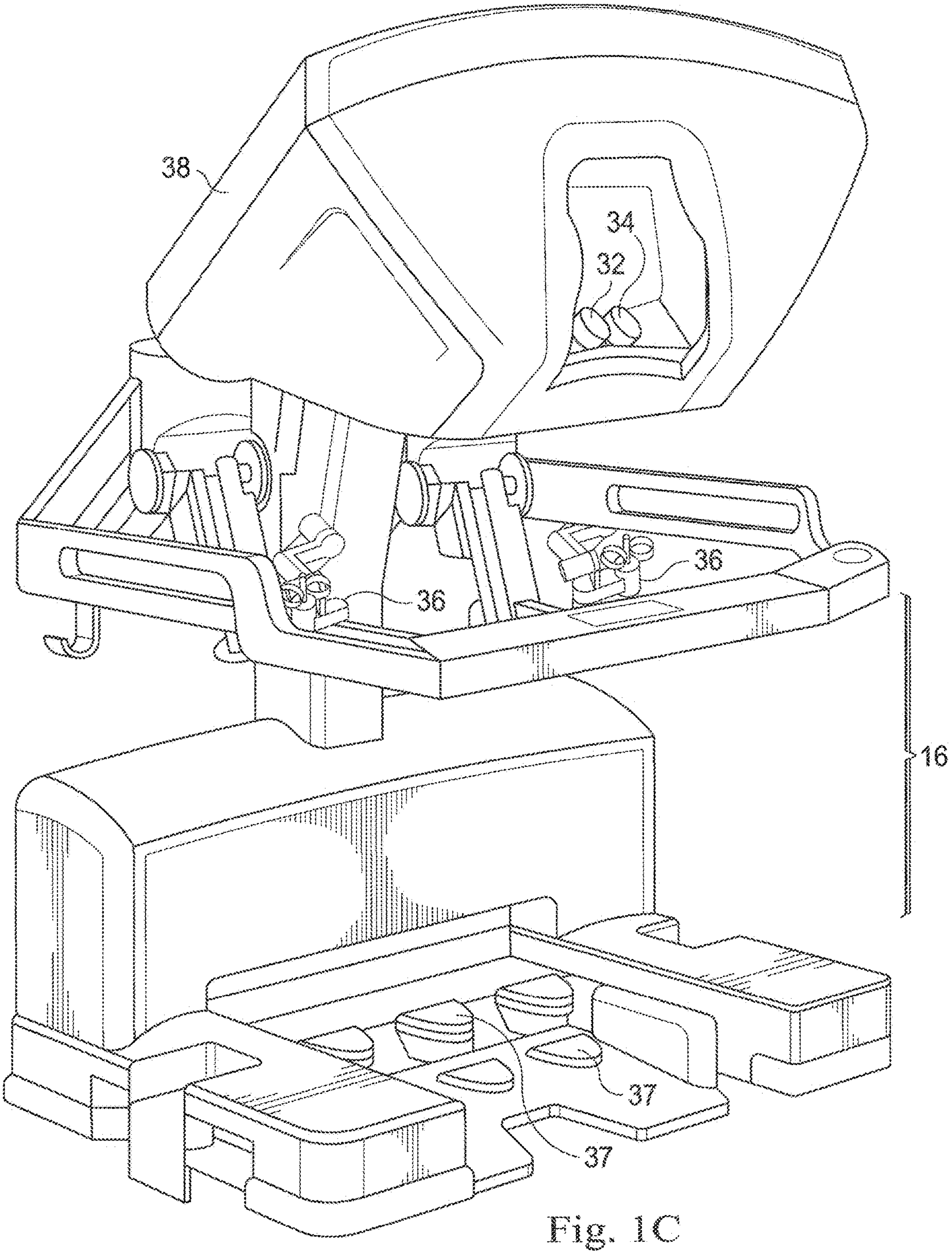
FIG. 1C is a perspective view of an operator's control console for a robotic medical system, in accordance with an embodiment of the present disclosure.

FIG. 1C is a perspective view of the operator's console 38. The operator's console 38 includes a left eye display 32 and a right eye display 34 for presenting the operator S with a coordinated stereo view of the surgical environment that enables depth perception. An operator input system 16 of the operator's console 38 includes one or more input control devices 36, which in turn causes the manipulator assembly 12 to manipulate one or more medical tools 14 and/or 15. The input control devices 36 may be used to, for example, close grasping jaw end effectors, apply an electrical potential to an electrode, deliver a medicinal treatment, or the like. In various alternatives, the input control devices 36 may additionally or alternatively include joystick devices, trackballs, data gloves, trigger-guns, hand-operated controllers, voice recognition devices, touch screens, body motion or presence sensors, and the like. In some embodiments, the input control devices 36 will provide the same degrees of freedom as their associated medical tools 14 to provide the operator S with telepresence, or the perception that the input control devices 36 are integral with the tools 14 so that the operator S has a sense of directly controlling the tools 14. In other embodiments, the input control devices 36 may have more or fewer degrees of freedom than the associated medical tools and still provide the operator S with telepresence. To this end, position, force, and tactile feedback sensors (not shown) may be employed to transmit position, force, and tactile sensations from the tools 14 back to the operator S's hands through the input control devices 36. Input control devices 37 are foot pedals that receive input from a user's foot.

As discussed above, physical compliance in a combination of a robotic arm assembly and a tool may cause under-damped vibrations and long settling times. In a system where the robotic arm assembly is flexible (e.g., including flexible joints) and/or with unbalanced link masses and inertias, motions commanded by the operator using an operator input system may cause such vibrations. While performing a medical or non-medical procedure, such vibrations experienced on the manipulator or a tool supported by the manipulator may cause control problems. For example, in a surgical procedure, such vibrations experienced on a tip of a medical tool may cause control problems. As a specific example, such vibrations may make it difficult for the system to perform, and clinicians to command, the desired manipulations of tissue, needles, and sutures. As discussed in detail below, by using both motor side measurement data from motor side sensors (e.g., joint encoders) and load-side measurement data from load side sensors (e.g., sensors located at links of the robotic arm assembly, at tool bodies, and/or at end effectors), a master/slave system may control the robotic arm assembly such that those vibrations are reduced (e.g. smaller vibration amplitudes, faster settling times, etc.).

Referring to FIGS. 2A, 2B, and 2C, in various embodiments, a load side sensor system may be attached to different load side locations (e.g., on the links of the robotic arm assembly, a tool supported by the robotic arm assembly, or on the end effector(s) of the tool) of a robotic system. Such a load side sensor system may provide to the control system (e.g. the control system 20 for the example of FIGS. 1A-1C) measurement data of the load side location, including, for example, the position and motion (e.g., linear velocity, linear acceleration, angular velocity) of the load side location. The control system may use the load side measurement data to control the robotic arm assembly to reduce tip vibration and settling time.

FIG. 2A shows an arm 200 (e.g., an arm 54) with an interchangeable tool 250 mounted thereon. The tool 250 may also be referred herein as a slave tool 250. In some embodiments, the tool 250 may be configured for manipulating industrial work pieces, or to manipulate human or animal tissue for reasons other than medical treatment or diagnosis. In some embodiments, the tool 250 may comprise a tool for performing medical procedures. The tool 250 includes a mounting portion 252 and a shaft 254. In the example shown in FIGS. 2A-2C, the mounting portion 252 comprises a mount located on a proximal portion of the tool 250. The mount is configured for removeably coupling the tool 250 to a carriage 253 of the manipulator. The shaft 254 is coupled to an end effector 260 using a wrist 258. The end effector 260 has a tool tip 262. In some embodiments, the arm 200 may include a support for a port device (e.g. a cannula for some medical procedures) that limits movement of the tool 250 relative to the arm 200. The tool 250 associated with each arm 200 may also be controlled by the operator at an operator input system (e.g. the operator input system 16 for the example of FIGS. 1A-IC).

In more detail, the arm 200 includes a vertical setup link 202 connected via a setup joint 204 to a distal-most setup link 206, and a manipulator arm portion 207 (e.g., manipulator arm 51 for the example of FIGS. 1A-1C) connected to the distal-most setup link 206. The manipulator arm portion 207 may also be referred herein as a slave manipulator portion 207. The manipulator arm portion 207 includes a yaw joint 208, a parallelogram pitch mechanism 210, and a spar 214. The yaw joint 208 connects the distal-most setup link 206 to the parallelogram pitch mechanism 210. The parallelogram pitch mechanism 210 includes a plurality of pitch joints 212*a*, 212*b*, 212*c* and links connecting those pitch joints. A spar 214 connects to the parallelogram pitch mechanism 210 at a spar joint 216. The tool 250's mounting portion 252 is mounted on the spar 214.

Each of the setup joint 204, the yaw joint 208, the pitch joints 212*a*, 212*b*, 212*c*, and the spar joint 216 are controlled by motors, referenced herein as a setup joint motor, a yaw joint motor, pitch joint motors, a spar joint motor. The arm 200 may also include an insertion gear 218 that provides insertion and withdrawal motion. Accordingly, at least parts of the arm 200 are configured to move in a completely motorized fashion. In this embodiment, the motors are under the control of the control system (e.g., the control system 20) and may be operated with motors of the other arms to take desired poses that may assist with advancing over a work piece (or a patient in a medical procedure), mounting of tools, preparation steps, or storage, among other activities. In addition, encoders and other sensors associated with each motor or joint provide feedback to the control system so that the control system receives data about, senses or detects, or determines the position, status, and setup of the arm 200.

In some embodiments, the arm 200 is mechanically constrained so that it moves the tool 250 around a stationary remote center of motion 256 (also called "remote center 256"). In some embodiments, the remote center of motion 256 is coincident with a shaft of a tool mounted to the arm 200. The yaw joint motor provides yaw motion around the remote center 256, and the pitch joint motor and spar joint motor may provide pitch motion around remote center 256. For minimally invasive medical procedures, typically the remote center of motion 256 is often locked at the incision in the patient's body wall during the procedure, and yaw and pitch motions about the remote center of motion 256 are allowed to carry out the intended surgical task. Alternatively, the remote center of motion may be located outside of the body to allow a greater range of motion without contacting the patient. For various procedures, the remote center of motion 256 can be located at any appropriate location for the procedure, such as at a location within a natural orifice or lumen during some medical procedures, a convenient location proximate a work piece during non-medical procedures, etc. Knowledgeable persons will understand that motion around a remote center of motion may be constrained by the use of software or by a physical constraint defined by a mechanical assembly.

Although each of the yaw joint 208, pitch joints 212*a*, 212*b*, 212*c*, spar joint 216 and insertion gear 218 may be controlled by an individual joint or gear controller, the joint and gear controllers may be controlled by a common joint control unit of a common control system 20 (e.g., a master/slave control system), so that the tool 250, the tip or end effector of the tool 250, and the manipulator arm portion 207 may be controlled through user (e.g., Operator S) manipulation of its associated control device (e.g., the operator input system for the example of FIGS. 1A-1C).

In the example of FIG. 2A, a load side sensor system 264 is attached to a load side location 266 of the spar 214, which is the last link of the manipulator arm portion 207. In the particular example of FIG. 2A, a distance D is between the load side location 266 and the spar joint 216. In various examples, the load side location 266 may be located at any portion of the spar 214. The load side sensor system 264 may include one or more sensors including, for example, an inertial measurement unit (IMU), an electromagnetic sensor, a shape sensor, a torque sensor, an optical tracking system, an image tracking system, a hybrid sensor system, other suitable sensor systems, and a combination thereof. In some examples, the IMU may include an accelerometer configured to measure the linear acceleration of the load side location 266 and a gyroscope configured to measure the angular velocity of the load side location 266. In some examples, the IMU may include a magnetometer configured to measure magnetism at the load side location 266.

As illustrated in FIGS. 2B and 2C, the load side sensor system 264 may be located at load side locations on various portions of the arm 200, tool 250 held by the arm 200, and/or end effectors 260 coupled to the tool 250. In the example of FIG. 2B, the load side sensor system 264 is be located at a load side location 266 at a proximal end of the tool 250 (e.g., on a mounting portion 252). In other examples, the load side sensor system 264 may be located at any portion of the tool 250, including for example, middle of a shaft and a distal end of the tool 250.

In the example of FIG. 2C, the load side sensor system 264 may be located at a load side location 266 (also referred to as a sensor portion 266) that is on the end effector 260. The load side sensor system 264 may be located at a load side location 266 on other portions of the arm 200, including, for example, links of the parallelogram pitch mechanism 210.

As shown in the examples of FIGS. 2A, 2B and 2C, different tools 250 and/or end effectors 260 may be mounted to the arm 200 to perform different functions. In the example of FIG. 2A, because the load side sensor system 264 is attached to the manipulator arm portion 207, such a single load side sensor system 264 may be used with different tools 250 and/or end effectors 260. On the other hand, in the examples of FIGS. 2B and 2C, to provide load side measurement data, a load side sensor system 264 may be required to be attached to each of those tools 250 and/or end effectors 260. As such, using a load side sensor system 264 attached to the manipulator arm portion 207 as shown in FIG. 2A may be more cost effective. In some embodiments, the location of the load side sensor system 264 may be determined based on various requirements of the system. In some examples, a load side sensor system 264 is located (e.g., at the manipulator arm portion 207) closer to the motors to improve controllability and allow for higher bandwidth (more aggressive) disturbance rejection. In other examples, a load side sensor system 264 is located (e.g., at the tool 250 or end effector 260) closer to the object (e.g., the tool tip) being controlled to improve the detection of the disturbances and the observability of the tool tip's state.

However, in embodiments where the load side sensor system 264 is not collocated with the tool tip, the control system (e.g. the control system 20 for the example of FIGS. 1A-1C) may not adjust a tool tip state estimate based on the load side sensor system 264 by simply combining the measurement data from the load side sensor system 264 and a state estimate of the based on the motor side encoders. As described below with reference to FIGS. 3, 4A, 4B and 5, to address this challenge, a control system (e.g. the control system 20 for the example of FIGS. 1A-1C) may use both a fusion block and a dynamic model to generate the tool tip position and motion estimates. By utilizing measurement data from both motor side and load side sensors while accounting for the dynamics between the load side location 266 and the tool tip 262, more accurate tool tip position and motion estimates may be achieved for better tool tip control with reduced vibrations and less settling time.

Referring to FIG. 3, illustrated therein is an example of a control system 300 (e.g., control system 20 for the example of FIGS. 1A-1C). The control system 300 may be used to control movement of the slave manipulator 207 portion of the arm 200 and consequently, the pose and motion of its attached tool 250 and end effector 260, as commanded by movement of an operator input system (e.g. operator input system 16 for the example of FIGS. 1A-1C) by an operator. In the description below, the control system 300 is also referred as a master/slave control system 300.

Both the master input device and slave manipulators may include a number of links connected by joints so as to facilitate multiple degrees-of-freedom movement. As the operator S moves the operator input system from one position to another during the course of performing a surgical procedure, sensors associated with the operator input system joints provide information indicating such command movement in the joint space of the master input device (the "master joint space,") and sensors associated with the slave manipulator joints provide information indicating slave manipulator movement (and consequently, the tool 250 movement) in slave joint space for feedback purposes. In order to better detect and control fine movements of their respective joints (e.g., in the target velocity range of 0.0005 to 0.01 radians per second at the joint, including the motion during the transition from zero velocity to the velocity in the target range), high resolution encoders may be used for the motor side sensors.

A master input processing unit 301 receives the information of the master joint positions, which are sampled at a control system processing rate (e.g., 1300 Hz), from the master joint encoders in the operator input system, and computes joint velocities from the sensed joint positions. A master forward kinematics processing unit 302 receives the master joint positions and velocities from the master input processing unit 301, and transforms them from master joint space to corresponding positions and velocities of the master frame (i.e., the frame associated with the operator input system) in Cartesian space relative to an operator reference frame. In some embodiments, the master forward kinematics processing unit 302 accomplishes this transformation by using a Jacobian and reference frame related information. Example operator reference frames that may be used include the eye reference frame (i.e., the reference frame associated with the position of the operator's eyes).

A scale and offset processing unit 304 receives the Cartesian position and velocity commands from the master forward kinematics processing unit 302, scales the commanded movement according to a scale factor selected to perform the procedure, and takes into account offsets to generate desired slave tool frame (i.e., the frame associated with the tool 250) positions and velocities. The scale adjustment is useful where small movements of the slave manipulator portion 207 of the arm 200 are desired relative to the larger movement of the operator input system 16 in order to allow more precise movement of the tool 250 at the procedure site. The offsets, on the other hand, determine, for example, the corresponding position and/or orientation of an end effector frame (e.g., the frame associated with an end effector 260 at the distal end of the tool 250) in the camera reference frame (i.e., the frame associated with the distal tip of the endoscope) relative to a position and orientation of the master frame in the eye reference frame.

A simulated slave processing unit 308 receives desired slave tool frame position and velocity commands from the scale and offset processing unit 304, and limits the desired slave tool frame position, orientation and velocities, to assigned Cartesian limits for instance to enforce correct and intuitive operation of the tool 250 by keeping it within its dexterous workspace. The simulated slave processing unit 308 generates simulated slave joint positions and velocities corresponding to the limited slave tool frame positions and velocities, while making sure that the generated slave joint positions and velocities do not exceed the actual slave joint's range of motion and maximum velocities (i.e., joint limits) even in the vicinity of kinematic singularities for the slave kinematics.

An inverse scale and offset processing unit 306 receives the simulated joint position and velocity commands from the simulated slave processing unit 308, and performs an inverse function (inverse to that of the scale and offset processing unit 304) on them. A Cartesian controller 307 receives the inputs to the scale and offset processing unit 304 as first inputs, and the outputs of the inverse scale and offset processing unit 306 as second inputs. The Cartesian controller 307 then generates an error signal as a difference between the first and second inputs, and a Cartesian force "$F_{CART}$" from the error signal such as with the following formula:

$$F_{CART} = K(\Delta x) + B(\Delta \dot{x}) \tag{1}$$

where "K" is a spring constant, "B" is a damping constant, "$\Delta\dot{x}$" is the difference between the Cartesian velocity inputs to the Cartesian controller 307 and "$\Delta x$" is the difference between the Cartesian position inputs to the Cartesian controller 307. For an orientation error, a corresponding torque in Cartesian space is determined.

A master transpose kinematics processing unit 315 receives the Cartesian force $F_{CART}$ through a summation node 314, and generates a corresponding torque in joint space using, for example, the Jacobian transpose matrix and kinematic relationships associated with the operator input system. In systems where the operator input system has motor-driven joints for range-of-motion limits or force feedback, a master output processing unit 316 receives the master torque signals from the master transpose kinematics processing unit 315, generates electrical currents corresponding to the master torque signals, and supplies the electrical currents to corresponding master joint motors of the operator input system (e.g. the operator input system 16 of the example of FIGS. 1A-1C). As a result, an operator S operating such an motor-driven operator input system (e.g. the operator input system 16) feels the Cartesian force, $F_{CART}$, whenever the operator S is commanding a position or velocity which exceeds system Cartesian or slave joint limits, or would result in a kinematic singularity condition for the slave manipulator portion 207 of the arm 200.

As the master input processing unit 301 is receiving master joint positions from sensors in the operator input system, a slave input processing unit 309 is also receiving slave positions from sensors in the slave manipulator portion 207 at the control system processing rate. The slave input processing unit 309 includes a motor side input processing unit 320 receiving slave joint measurement data (e.g., slave joint positions and motions data) from motor side sensors (e.g., joint encoders), and a load side input processing unit 322 receiving slave load side measurement data (e.g., positions and motions data of the load side location 266) from load side sensors (e.g., the load side sensor system 264). A joint control unit 318 receives the slave joint measurement data and the slave load side measurement data from the slave input processing unit 309 and the simulated joint commands provided from the simulated slave processing unit 308, and generates slave torque command signals for the slave joint motors and master torque feedback command signals for the master joint motors.

The slave torque command signals are generated by the joint control unit 318 so as to drive joints of the slave manipulator until feedback errors calculated in the joint control unit 318 zero out. A slave output processing unit 310 receives the slave torque command signals from the joint control unit 318, converts them into appropriate electrical currents, and supplies the electrical currents to the joint motors of the slave manipulator so as to drive the motors accordingly.

In some embodiments, the master torque feedback command signals are generated by the joint control unit 318 which reflect forces being exerted against the tool 250, or against the slave manipulator supporting the tool 250, back to the operator input system (e.g. the operator input system 16) so that they may be felt in some form by the operator S. In some embodiments, the joint control unit 318 generates the master torque feedback command signals based on the slave joint position and velocity tracking errors. In various embodiments, the slave tracking error may be determined using motor side tracking error, tool tip tracking error determined by the forward kinematics and the motor positions, tool tip tracking error determined using the load side sensor system 264, load-side tracking error from joint positions and velocities estimated using the load side sensor system 264, and/or any combination thereof. In some embodiments, the joint control unit 318 generates the master torque feedback command signals based on measurement data from both the slave joint encoders and the load side sensor system 264. A kinematic mapping unit 311 receives the master torque feedback command signals from the joint control unit 318, and generates the corresponding Cartesian force at the tip of the tool 250 relative to the camera frame of the endoscope using the slave kinematic configuration and the previously calculated slave fulcrum (e.g., remote center 256) position information.

A gain 313 adjusts the magnitude of the Cartesian force so as to ensure system stability while providing adequate force sensation to the operator S. The gain adjusted Cartesian force is then passed through the summation node 314, and processed along with the Cartesian force provided by the Cartesian controller 307 through the master transpose kinematics processing unit 315 and master output processing 316 as previously described in reference to their processing of the Cartesian force provided by the Cartesian controller 307.

The joint control unit 318 includes a joint controller for each active joint of the slave manipulator portion 207 of the arm 200 that is being controlled by the master/slave control system 300. In particular, where the slave manipulator portion 207 includes a yaw joint 208, pitch joints 212*a*, 212*b*, 212*c*, spar joint 216, and an insertion gear 218, such as the arm 200 for the examples of FIGS. 2A, 2B, and 2C, each of these joints or gears may have its own controller, as will each of the drivable mechanical elements for the tool wrist and end effector mechanisms.

FIG. 4 illustrates, as an example, a block diagram of a joint controller unit 318 (e.g., for controlling movement of the yaw joint 208, pitch joints 212*a*, 212*b*, 212*c*, spar joint 216, and insertion gear 218 of the slave manipulator portion 207, or any one or more of several drivable mechanical elements for manipulating a tool wrist or end effector mechanism). To simplify the description herein and in the claims, the term "joint" is to be understood to include the joint drive train possibly including cables, pulleys, gears, spools, and any other drivable mechanical element that may be used in controlling degrees of freedom movement or other mechanical action associated with tools or the slave manipulators or robotic arms holding and/or moving the tools. This can be for performing non-medical or medical procedures. Example medical procedures include, for example, biopsies, imaging procedures, diagnostic procedures, and surgical procedures such as minimally invasive laparoscopic or endoluminal surgery.

As discussed in detail below, the joint controller unit 318 may use a fusion block to generate a fused estimate of the position and motion of the load side location 266 by fusing both motor side measurement data and load side measurement data. As such, the fused estimate of the load side location 266 may be more accurate than an estimate based on motor side measurement data alone, which may result in a more accurate estimate of the position and motion of the tool tip 262. Furthermore, in embodiments where the load side sensor system 264 is not collocated with the tool tip 262, the joint controller unit 318 may account for the dynamics between the load side location 266 and the tool tip 262 and the dynamics of the load side sensor system 264 using corresponding dynamic models. This may further improve the accuracy of the estimate of the position and motion the tool tip 262, thereby enabling better control of the tool tip.

The joint controller unit 318 includes a forward kinematics block 402 that receives joint encoder data 404 (denoted as $\Theta_{enc}$) from the motor side input processing unit 320 (e.g., provided by joint encoders in the slave manipulator portion 207). The joint encoder data 404 $\Theta_{enc}$ may include joint position data, joint motion (e.g., velocity, acceleration) data, or a combination thereof. In various embodiments, kinematics equations of the kinematic chains that form the manipulator arm portion 207 may be used to map the joint parameters to the configuration of the robot system. The dimensions of the manipulator arm portion 207 and its associated kinematic equations define the volume of space reachable by the manipulator arm portion 207 and the features associated with the manipulator arm portion 207, known commonly as the workspace. The forward kinematics block 402 may use forward kinematics to compute the position of a particular feature (e.g., links of the manipulator arm portion 207 including the spar 214, tool 250, end effector 260, tool tip 262) associated with the manipulator arm portion 207 in the workspace.

In some embodiments, the forward kinematics block 402 may apply forward kinematics associated with the manipulator arm portion 207 to the joint encoder data 404 $\Theta_{enc}$, and generate an estimate 406 (denoted as $$T_{sensor}^{(enc)})$$

for the position and/or motion (e.g., velocity, acceleration) of the load side location 266. In an example, the forward kinematics block 402 may transform the joint encoder data 404 $\eta_{enc}$ (e.g., using a Cartesian transform) from the world reference frame to the load side sensor system frame (e.g., the frame associated with the load side sensor system 264). In examples where the estimate 406

$$T_{sensor}^{(enc)}$$

includes a velocity estimate of the load side location 266, the forward kinematics block 402 may apply a Jacobian function 430 to the corresponding joint velocity data in the joint encoder data 404 $\Theta_{enc}$ to generate the velocity estimate of the load side location 266.

As illustrated in the example of FIG. 4, the estimate 406

$$T_{sensor}^{(enc)}$$

sensor of the load side location 266 based on joint encoder data 404 $\Theta_{enc}$ is sent to a fusion block 408. The fusion block 408 includes a state estimator 410 and a dynamic model unit 412. The state estimator 410 may receive load side measurement data 414 of a load side location 266 from the load side input processing unit 322 (e.g., provided by the load side sensor system 264). In an example, the load side measurement data 414 may include linear acceleration data $\ddot{x}$ and angular velocity data $\omega$ of the load side location 266, denoted as $$\begin{bmatrix} \ddot{x} \\ \omega \end{bmatrix}_{sensor}.$$

In the example of FIG. 4, the state estimator 410 may receive the estimate 406

$$T_{sensor}^{(enc)}$$

and measurement data 414

$$\begin{bmatrix} \ddot{x} \\ \omega \end{bmatrix}_{sensor}$$

associated with the load side location 266, and generate a fused state estimate Cartesian transform 416 (denoted as $$T_{sensor}^{(fus)})$$

for the load side location 266. The fused state estimate 416

$$T_{sensor}^{(fus)}$$

may include estimates for the position/motion of the load side location 266. Various state estimator algorithms may be used to generate the fused state estimate 416

$$T_{sensor}^{(fus)},$$

including, for example, Kalman filter and its variants (e.g., extended Kalman filter, unscented Kalman filter, steady-state Kalman filter, etc.), $H_\infty$ filter, particle filter, Luenberger observer, Madgwick filter, Alpha-beta-gamma filter, sliding-mode observer, etc. By using a fusion block to combining the estimate 406

$$T_{sensor}^{(enc)}$$

sensor generated based on the joint encoder data 404 $\Theta_{enc}$ and the measurement data 414 from the load side sensor system 264, the position and motion of the load side location 266 is better captured than the estimate 406

$$T_{sensor}^{(enc)}$$

generated using the joint encoder data 404 $\Theta_{enc}$ alone.

In some embodiments, the load side sensor system 264 is not collocated with the tool tip 262. For example, the load side sensor system 264 may be located at a link (e.g., at a spar 214) of the manipulator arm portion 207 or a tool 250 (e.g., at a mounting portion 252 of the tool 250). In such embodiments, the fusion block 408 of the joint controller unit 318 may include a dynamic model unit 412 to account for the dynamics between the load side location 266 and the tool tip 262. As shown in the example of FIG. 4, the state estimator 410 may send the fused state estimate 416

$$T_{sensor}^{(fus)}$$

of the load side location 266 to a dynamic model unit 412. The dynamic model unit 412 determines a dynamic model that models the dynamics between the load side location 266 and the tool tip 262. In various embodiments, the dynamic model may be determined based on the position of the load side location 266, various physical properties of the arm 200, body of tool 250, and end effector 260, including, for example, mass, stiffness, friction, damping, elastic deformation of bearings and gears, deflection of the links under load, vibrations, etc. The dynamic model may be derived from physical modeling of individual components, experimental identification of dynamics, a combination of derivation and empirical data, and/or on-line adaptive identification of dynamics. The dynamic model unit 412 may produce a Cartesian transform from the world reference frame to the tool tip reference frame (e.g., the frame associated with the tool tip 262), and generate a fused state estimate Cartesian transform 418

$$T_{tip}^{(fus)}$$

of the tool tip 262 based on the dynamic model and the fused state estimate 416

$$T_{sensor}^{(fus)}$$

of the load side location 266. The fusion block 408 may then output the fused state estimate 418

$$T_{tip}^{(fus)}$$

tip of the tool tip 262.

In some embodiments, the fused state estimate 418

$$T_{tip}^{(fus)}$$

of the tool tip 262 and the fused state estimate 416

$$T_{sensor}^{(fus)}$$

of the load side location 266 may include estimates for the same state parameters (e.g., position, velocity, or a combination thereof). In an example, each of the fused state estimate 418

$$T_{tip}^{(fus)}$$

of the tool tip 262 and the fused state estimate 416

$$T_{sensor}^{(fus)}$$

of the load side location 266 only includes a position estimate, and does not include any motion (e.g., velocity) estimate. In another example, each of the fused state estimate 418

$$T_{tip}^{(fus)}$$

of the tool tip 262 and the fused state estimate 416

$$T_{sensor}^{(fus)}$$

of the load side location 266 includes a velocity estimate, and does not include a position estimate. In yet another example, each of the fused state estimate 418

$$T_{tip}^{(fus)}$$

of the tool tip 262 and the fused state estimate 416

$$T_{sensor}^{(fus)}$$

of the load side point 266 includes estimates for both the position and velocity.

In some embodiments, the forward kinematics block 402 may apply forward kinematics associated with the manipulator arm 207, the tool 250, and the end effector 260 to the joint encoder data 404 $\Theta_{enc}$, and generate a state estimate 420 (denoted as $$T_{tip}^{(enc)})$$

for the tool tip 262 based on the joint encoder data 404 $\Theta_{enc}$. The forward kinematics block 402 may transform the joint encoder data 404 $\Theta_{enc}$ (e.g., using a Cartesian transform) from the world reference frame to the tool tip reference frame. The state estimate 420

$$T_{tip}^{(enc)}$$

may include estimates for the position/motion of the tool tip 262. In some examples, the forward kinematics block 402 may use a Jacobian function 430 to generate the velocity estimate of the tool tip 262 based on the joint velocity data in the joint encoder data 404 $\Theta_{enc}$.

In some embodiments, the joint controller unit 318 includes a comparator 422. The comparator 422 receives the fused state estimate 418

$$T_{tip}^{(fus)}$$

of the tool tip 262 from the fusion block 408, and the state estimate 420

$$T_{tip}^{(enc)}$$

of the tool tip 262 from the forward kinematics block 402, and generates a tool tip state estimate difference 424 $\delta T_{tip}$ between $$T_{tip}^{(fus)} \text{ and } T_{tip}^{(enc)}.$$

The tool tip state estimate difference 424 $\delta T_{tip}$ may include a position estimate difference of the tool tip 262, a velocity estimate difference of the tool tip 262, or a combination of both.

As illustrated in FIG. 4A, the joint controller unit 318 may include an inverse kinematics block 426. The inverse kinematics block 426 may receive the tool tip state estimate difference 424 $\delta T_{tip}$ from the comparator 422, and receive the join encoder data @ enc from the joint encoders 401. The inverse kinematic block 426 may apply inverse kinematics for converting the tool tip state estimate difference 424 $\delta T_{tip}$ to a joint adjustment estimate 432 (denoted as $\delta\Theta_{CMD}$). The joint adjustment estimate 432 $\delta\Theta_{CMD}$ may include estimates of the joint position and/or motion (e.g., velocity) adjustments that are needed to compensate for the tool tip state estimate difference 424 $\delta T_{tip}$. In some examples, the inverse kinematics block 426 may use an inverse Jacobian function 428 to generate the estimate of the joint velocity adjustment based on a tool tip velocity estimate difference in the tool tip state estimate difference 424 $\delta T_{tip}$.

The joint adjustment estimate 432 $\delta\Theta_{CMD}$ may be sent to a combiner 434, which combine a commanded joint data 436 (denoted as $\Theta'_{CMD}$) and the joint adjustment estimate 432 $\delta\Theta_{CMD}$ to generate adjusted commanded joint data 438 (denoted as $\Theta_{CMD}$). In an example, the commanded joint data 436 $\Theta'_{CMD}$ is provided by the simulated slave processing unit 308 in response to inputs from the operator input system (e.g. operator input system 16 in the FIGS. 1A-1C example). The adjusted commanded joint data 438 $\Theta_{CMD}$ may include an adjusted commanded joint position, an adjusted commanded joint velocity, or a combination of both.

In some embodiments, the joint control unit 318 may generate slave torque command signals based on the tool tip state estimate difference 424 $\delta T_{tip}$. By using the tool tip state estimate difference 424 $\delta T_{tip}$, the joint control unit 318 generates the slave torque command signals that accounts for the tool tip state estimate difference 424 $\delta T_{tip}$. The slave torque command signals may be used to drive motors (e.g., motors for yaw joint 208, pitch joints 212*a*, 212*b*, and 212*c*, spar joint 216, insertion gear 218) of the slave manipulator 207.

In various embodiments, the joint control unit 318 may use a feedback controller for controlling the slave joint motors. The feedback controller may include a proportional-derivative (PD) controller, proportional-integral-derivative (PID) controller, any linear controller (e.g., a lead-lag controller, an H, controller, an LQR/LQG controller), a linear-parameter-varying controller, a sliding-mode or other adaptive controller, and any other suitable feedback controllers. The slave torque command signals may be used to drive joints of the slave manipulator until feedback errors calculated by the feedback controller zero out.

In some embodiments, the slave torque command signals may be further adjusted by a torque saturation block, which may limit the commanded torque values so that the commanded torque values do not exceed maximum the desired torque values for their respective motors.

Referring to FIG. 4B, illustrated therein is a joint control unit 450 (e.g., joint control unit 318 of FIG. 3) that uses link data provided by the link sensor systems to feedback a joint acceleration feedback error. The joint control unit 450 is substantially similar to the joint control unit 400 of FIG. 3A other than the distinctions described below. As shown in FIG. 4B, a multi-variable controller 452 (e.g., a multi-variable H, controller) may receive the joint adjustment estimate 432 (e.g., from the inverse kinematics block 426), receive a commanded joint data 436 $\Theta'_{CMD}$ (e.g., from the simulated slave processing unit 308), and receive a joint encoder data 404 $\Theta_{enc}$ (e.g., from the motor side input processing unit 320). The multi-variable controller 452 may generate a motor torque command based on the joint adjustment estimate 432, commanded joint data 436, and joint encoder data 404. A slave output processing unit 310 receives the slave torque command signal from the multi-variable controller 452, converts it into appropriate electrical currents, and supplies the electrical currents to the joint motors of the slave manipulator so as to drive the motors accordingly.

FIG. 5 illustrates a method 500 for controlling the tool tip based on measurement data from both motor-side sensors (e.g., joint encoders) and load-side sensors. The method 500 is illustrated in FIG. 5 as a set of operations or processes 502 through 514. Not all of the illustrated processes 502 through 514 may be performed in all embodiments of method 500. Additionally, one or more processes that are not expressly illustrated in FIG. 5 may be included before, after, in between, or as part of the processes 502 through 514. In some embodiments, one or more of the processes may be implemented, at least in part, in the form of executable code stored on non-transitory, tangible, machine-readable media that when run by one or more processors (e.g., the processors of control system) may cause the one or more processors to perform one or more of the processes.

As shown in the method 500, a joint controller may control the movement of the joints of a manipulator arm based on measurement data from both motor side sensors and load side sensors. In some embodiments, the load-side sensors may be located at a load side location on links of the manipulator arm or other locations (e.g., a tool supported by a distal portion of the manipulator arm) that are not collocated with the distal tool tip. In those embodiments, the joint controller may include a dynamic model unit to account for the dynamics between the load side location and the tool tip. By utilizing both measurement data from both motor side sensors and load side sensors and accounting for the dynamics between the load side sensors and the tool tip, better tool tip control with reduced vibrations and less settling time is achieved.

The method 500 begins at process 502, where a joint controller receives motor side (e.g. joints) measurement data from joint encoders of a manipulator arm of a robotic system (e.g. the teleoperational medical system shown in FIGS. 1A-1C, a medical system, or a non-medical system). For example, the joint controller unit 318 of the master/slave control system 300 may receive joint measurement data from the joint encoders of the manipulator arm portion 207. The method 500 may proceed to process 504, where the joint controller generates a first tool tip estimate based on the joint measurement data without using any load side measurement data. For example, the forward kinematics block 402 of the joint controller unit 318 may apply forward kinematics to the joint measurement data to generate a first tool tip estimate. The method 500 may proceed to process 506, where the joint controller receives load side measurement data of a load side location from a load side sensor system. For example, a joint controller unit 318 may receive measurement data of a load side location 266 provided by a load side sensor system 264.

The method 500 may then proceed to process 508, where the joint controller generates an estimate of the position and motion of the load side location 266 based on both joint measurement data and the load side measurement data. At process 508, a joint controller unit 318 may use the forward kinematics block 402 to apply forward kinematics to the joint measurement data, and generate an estimate $$T_{sensor}^{(enc)}$$

for the position and/or motion of the load side location 266. A state estimator 410 may fuse the first estimate $$T_{sensor}^{(enc)}$$

with the load side measurement data (e.g., acceleration data and angular velocity data) of the load side location 266 to generate a fused estimate $$T_{sensor}^{(fus)}$$

of the load side location 266.

The method 500 may then proceed to process 510, where the joint controller generates a second tool tip estimate (a fused tool tip estimate) using the fused load side location estimate and a dynamic model. The dynamic model may be determined based on the dynamics of the manipulator arm, the tool coupled to the manipulator arm, and the end effector coupled to the tool. For example, at process 510, a dynamic model unit 412 may use the dynamic model to generate a fused tool tip estimate based on the fused load side location estimate provided by the state estimator 410.

The method 500 may then proceed to process 512, where the joint controller determines joint adjustment data based on a tool tip estimate difference between the first and second tool tip estimates. For example, at process 512, the joint controller unit 318 may determine a tool tip state estimate difference 424 by comparing the first and second tool tip estimates using a comparator 422. An inverse kinematics block 426 may apply inverse kinematics to the tool tip state estimate difference 424 to generate the corresponding joint adjustment data.

The method 500 may then proceed to process 514, where the joint controller may control motion of the joints based on the joint adjustment data. For example, at process 514, the joint controller unit 318 may adjust the commanded joint data $\Theta'_{CMD}$ (e.g., provided by the simulated slave processing unit 308 in response to inputs from the operator input system) using the joint adjustment data. The joint controller unit 318 may then generate slave torque command signals for controlling the joints of the manipulator arm based on the resulting tool tip state estimate difference 424, denoted as $\delta T_{tip}$. By using both motor side and load side measurement data and accounting for the dynamics between the load side sensor system and the tool tip, better tool tip control is achieved.

Any reference to surgical tools and surgical methods is non-limiting as the tools and methods described herein may be used for animals, human cadavers, animal cadavers, portions of human or animal anatomy, non-surgical diagnosis, industrial systems, and general robotic or teleoperational systems.

One or more elements in embodiments of the invention may be implemented in software to execute on a processor of a computer system such as control processing system. When implemented in software, the elements of the embodiments of the invention are essentially the code segments to perform the necessary tasks. The program or code segments can be stored in a processor-readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read-only memory (ROM), a flash memory, an erasable programmable read-only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A system comprising:
- a robotic manipulator configured for control of motion of a tool, the robotic manipulator including a joint and a link connected to the joint, wherein the link is configured to connect to a tool;
- a processing unit including one or more processors, the processing unit configured to:
- receive joint measurement data of the joint;
- receive load side measurement data from a sensor system located at the link;
- provide a dynamic model associated with dynamics between the sensor system and the tool;
- generate a first estimate of a first parameter of the tool using the joint measurement data, the load side measurement data, and the dynamic model; and
- control the joint based on the first estimate of the tool.

2. The system of claim 1, wherein the sensor system is located at a sensor portion of the link; and
- wherein the dynamic model is associated with dynamics between the sensor portion of the link and a tool tip of the tool.

3. The system of claim 2, wherein the dynamic model is determined based on physical properties of the link and the tool.

4. The system of claim 2, wherein the processing unit is configured to:
- generate a fused state estimate of the first parameter of the tool using the joint measurement data and the load side measurement data;
- generate, based on the dynamic model, a Cartesian transform from a world reference frame to a tool tip reference frame associated with the tool tip; and
- generate the first estimate of the first parameter of the tool by applying the Cartesian transform to the fused state estimate.

5. The system of claim 1, wherein to generate the first estimate, the processing unit is configured to:
- generate a sensor portion estimate of a first parameter of a sensor portion of the link using the joint measurement data and load side measurement data, wherein the sensor system is located at the sensor portion of the link; and
- generate the first estimate based on the sensor portion estimate and a dynamic model between the sensor portion and the tool.

6. The system of claim 5, wherein the sensor portion estimate is generated using a state estimator algorithm selected from the group consisting of a Kalman filter, a particle filter, a nonlinear observer, and an alpha-beta-gamma filter.

7. The system of claim 1, wherein the processing unit is further configured to:
- generate a second estimate of a second parameter of the tool using the joint measurement data,
  - wherein the first parameter of the tool is one of a position and a velocity of the tool,
  - wherein the second parameter of the tool is the other of the position and the velocity of the tool;
- generate a third estimate of the second parameter of the tool using the joint measurement data and load side measurement data; and
- control the joint based on the first estimate and a first difference between the second estimate and the third estimate.

8. The system of claim 1, wherein the joint measurement data includes data associated with at least one of a position and a velocity of the joint.

9. The system of claim 1, wherein the load side measurement data includes translational acceleration data and angular velocity data.

10. The system of claim 1, further comprising:
- an actuation assembly coupled to the joint to drive motion of the joint;
- wherein to control the joint based on the first estimate, the processing unit is configured to:
  - generate joint adjustment data based on the first estimate; and
  - generate a control signal based on the joint adjustment data for controlling the actuation assembly.

11. A method comprising:
- receiving joint measurement data of a joint of a robotic manipulator, the robotic manipulator including a link connected to the joint, wherein the link is configured to connect to a tool;
- receiving load side measurement data from a sensor system located at the link;
- providing a dynamic model associated with dynamics between the sensor system and a tool;
- generating a first estimate of a first parameter of the tool using the joint measurement data, the load side measurement data, and the dynamic model; and
- controlling the joint based on the first estimate of the tool.

12. The method of claim 11, wherein the sensor system is located at a sensor portion of the link; and
- wherein the dynamic model is associated with dynamics between the sensor portion of the link and a tool tip of the tool.

13. The method of claim 12, wherein the dynamic model is determined based on physical properties of the link and the tool.

14. The method of claim 12, further comprising:
- generating a fused state estimate of the first parameter of the tool using the joint measurement data and the load side measurement data;
- generating, based on the dynamic model, a Cartesian transform from a world reference frame to a tool tip reference frame associated with the tool tip; and
- generating the first estimate of the first parameter of the tool by applying the Cartesian transform to the fused state estimate.

15. The method of claim 11, further comprising:
- generating a sensor portion estimate of a first parameter of a sensor portion of the link using the joint measurement data and load side measurement data, wherein the sensor system is located at the sensor portion of the link; and
- generating the first estimate based on the sensor portion estimate and a dynamic model between the sensor portion and the tool.

16. The method of claim 15, wherein the sensor portion estimate is generated using a state estimator algorithm selected from the group consisting of a Kalman filter, a particle filter, a nonlinear observer, and an alpha-beta-gamma filter.

17. The method of claim 11, further comprising:

generating a second estimate of a second parameter of the tool using the joint measurement data, wherein the first parameter of the tool is one of a position and a velocity of the tool, wherein the second parameter of the tool is the other of the position and the velocity of the tool;

generating a third estimate of the second parameter of the tool using the joint measurement data and load side measurement data; and controlling the joint based on the first estimate and a first difference between the second estimate and the third estimate.

18. The method of claim 11, wherein the joint measurement data includes data associated with at least one of a position and a velocity of the joint.

19. The method of claim 11, further comprising:

generating joint adjustment data based on the first estimate; and generating a control signal based on the joint adjustment data for controlling an actuation assembly, wherein the actuation assembly is coupled to the joint to drive motion of the joint.

20. A non-transitory machine-readable medium comprising a plurality of machine-readable instructions which, when executed by one or more processors, are adapted to cause one or more processors to perform a method comprising:

receiving joint measurement data of a joint of a robotic manipulator, wherein the robotic manipulator includes a link connected to the joint, wherein the link is configured to connect to a tool;

receiving load side measurement data from a sensor system located at the link;

provide a dynamic model is associated with dynamics between the sensor system and a tool;

generate a first estimate of a first parameter of the tool using the joint measurement data, the load side measurement data, and the dynamic model; and control the joint based on the first estimate of the tool.

* * * * *